US009960325B2

(12) United States Patent
Fukunaga et al.

(10) Patent No.: US 9,960,325 B2
(45) Date of Patent: *May 1, 2018

(54) LEAD, WIRING MEMBER, PACKAGE PART, METAL PART PROVIDED WITH RESIN AND RESIN-SEALED SEMICONDUCTOR DEVICE, AND METHODS FOR PRODUCING SAME

(71) Applicant: PANASONIC INTELLECTUAL PROPERTY MANAGEMENT CO., LTD., Osaka (JP)

(72) Inventors: Takahiro Fukunaga, Kyoto (JP); Yasuko Imanishi, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 51 days.

This patent is subject to a terminal disclaimer.

(21) Appl. No.: 14/576,105

(22) Filed: Dec. 18, 2014

(65) Prior Publication Data

US 2015/0104657 A1 Apr. 16, 2015

Related U.S. Application Data

(62) Division of application No. 13/062,408, filed as application No. PCT/JP2009/007177 on Dec. 24, 2009, now Pat. No. 8,946,746.

(30) Foreign Application Priority Data

Dec. 25, 2008 (JP) .................... 2008-330788

(51) Int. Cl.
| | | |
|---|---|---|
| H01L 33/52 | (2010.01) | |
| C07D 249/12 | (2006.01) | |
| C07D 251/20 | (2006.01) | |
| C07D 251/38 | (2006.01) | |
| C07D 487/04 | (2006.01) | |
| C08G 61/10 | (2006.01) | |
| C23C 28/00 | (2006.01) | |
| H01L 23/29 | (2006.01) | |
| H01L 23/31 | (2006.01) | |
| H01L 23/00 | (2006.01) | |

(52) U.S. Cl.
CPC ............ *H01L 33/52* (2013.01); *C07D 249/12* (2013.01); *C07D 251/20* (2013.01); *C07D 251/38* (2013.01); *C07D 487/04* (2013.01); *C08G 61/10* (2013.01); *C23C 28/00* (2013.01); *H01L 23/296* (2013.01); *H01L 23/3142* (2013.01); *C08G 2261/1646* (2013.01); *C08G 2261/312* (2013.01); *C08G 2261/3221* (2013.01); *H01L 24/48* (2013.01); *H01L 2224/48091* (2013.01); *H01L 2224/48245* (2013.01); *H01L 2224/48247* (2013.01); *H01L 2224/73265* (2013.01); *H01L 2224/83192* (2013.01); *H01L 2224/92247* (2013.01); *H01L 2924/00014* (2013.01); *H01L 2924/01019* (2013.01); *H01L 2924/01037* (2013.01); *H01L 2924/07802* (2013.01); *H01L 2924/12041* (2013.01); *H01L 2924/12042* (2013.01); *H01L 2924/12044* (2013.01); *H01L 2924/14* (2013.01); *H01L 2924/1433* (2013.01); *H01L 2924/181* (2013.01); *Y10T 428/31678* (2015.04)

(58) Field of Classification Search
None
See application file for complete search history.

(56) References Cited

U.S. PATENT DOCUMENTS

| | | | |
|---|---|---|---|
| 4,212,880 A | 7/1980 | Fisher et al. | |
| 4,873,173 A * | 10/1989 | Sasaoka | G03C 5/30 430/264 |
| 5,759,874 A | 6/1998 | Okawa | |
| 7,749,782 B1 | 7/2010 | Knollenberg et al. | |

(Continued)

FOREIGN PATENT DOCUMENTS

| | | |
|---|---|---|
| EP | 0 010 440 A1 | 4/1980 |
| JP | 55-57590 | 4/1980 |

(Continued)

OTHER PUBLICATIONS

English translation of JP2005-132890, retrieved online Sep. 14, 2016.*
H. Zhong et al., "New Optoelectronic Materials Based on Bitriazines: Synthesis and Properties," Organic Letters, vol. 10, No. 5, pp. 709-712, 2008.
United States Notice of Allowance issued in U.S. Appl. No. 13/062,408 dated Sep. 19, 2014.

*Primary Examiner* — Samantha L Shterengarts
(74) *Attorney, Agent, or Firm* — McDermott Will & Emery LLP

(57) ABSTRACT

A semiconductor device and manufacturing method therefor, provided with the aims of constraining resin burr formation while having good electric connectivity and joining strength, and LED device, provided with the aim of improving adhesion between silicon resin and leads while having good luminescent characteristics. For these purposes, an organic film is formed through self-assembly by functional organic molecules at surface border regions of outer leads of a QFP. The functional organic molecules consist of a first functional group bonding with metals, a principal chain, and a second functional group inducing hardening in thermosetting resins. The principal chain consists of a glycol chain, or else of a glycol chain and one or more among methylene, fluoromethylene, or siloxane chains. The principal chain also preferably includes one or more among a hydroxyl radical, ketone, thioketone, primary amine, secondary amine, and aromatic compounds.

1 Claim, 19 Drawing Sheets

(56) References Cited

U.S. PATENT DOCUMENTS

| | | |
|---|---|---|
| 8,785,957 B2 | 7/2014 | Hata et al. |
| 2005/0006794 A1 | 1/2005 | Kashiwagi et al. |
| 2007/0212478 A1 | 9/2007 | Fukunaga et al. |

FOREIGN PATENT DOCUMENTS

| | | |
|---|---|---|
| JP | 55-058072 | 4/1980 |
| JP | 06-069366 | 3/1994 |
| JP | 07-183416 | 7/1995 |
| JP | 07-254622 | 10/1995 |
| JP | 10-329461 | 12/1998 |
| JP | 3076342 | 6/2000 |
| JP | 2001-144145 A | 5/2001 |
| JP | 2002-033345 A | 1/2002 |
| JP | 2004-200349 A | 7/2004 |
| JP | 2004-200350 A | 7/2004 |
| JP | 2005-042099 A | 2/2005 |
| JP | 2005-132890 A | 5/2005 |
| JP | 2007-266562 A | 10/2007 |

* cited by examiner

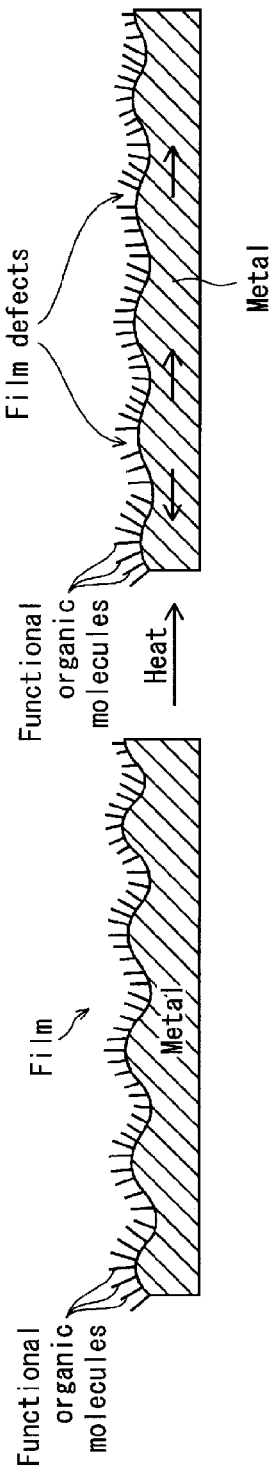
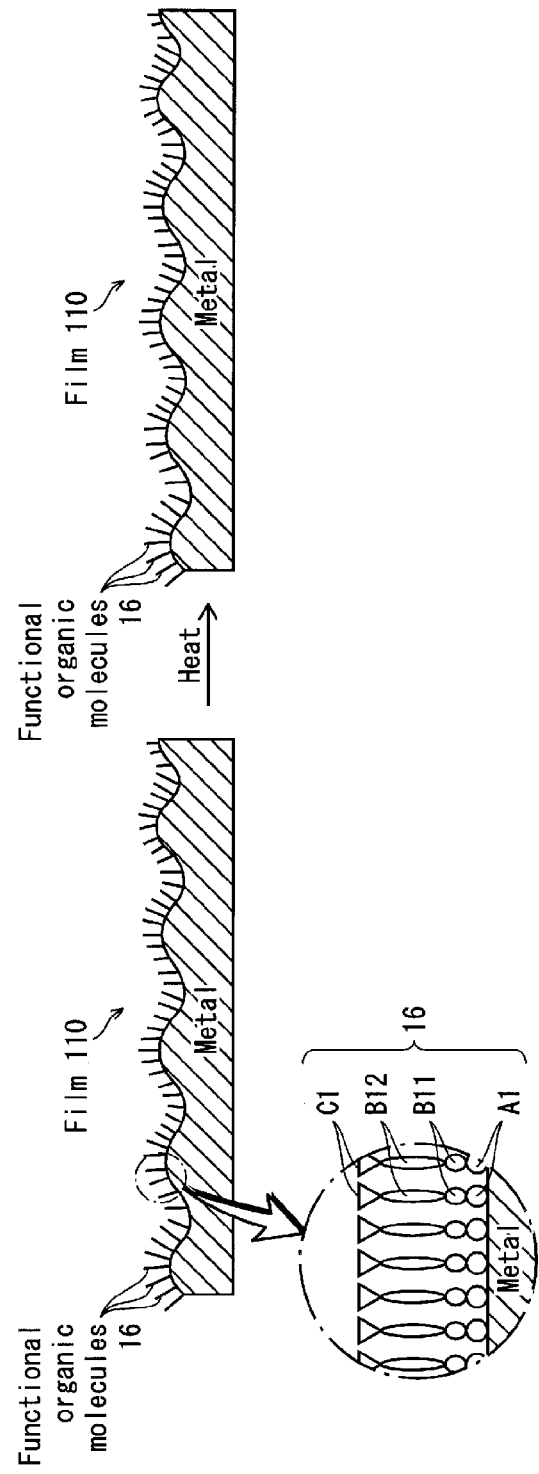

LEAD, WIRING MEMBER, PACKAGE PART, METAL PART PROVIDED WITH RESIN AND RESIN-SEALED SEMICONDUCTOR DEVICE, AND METHODS FOR PRODUCING SAME

Related Applications

This application is a Division of application Ser. No. 13/062,408 filed on Mar. 4, 2011, Now U.S. Pat. No. 8,946,746, which is the U.S. National Phase under 35 U.S.C. § 371 of International Application No. PCT/JP2009/007177, filed on Dec. 24, 2009, which in turn claims the benefit of Japanese Application No. 2008-330788, filed on Dec. 25, 2008, the disclosures of which Applications are incorporated by reference herein.

TECHNICAL FIELD

The present invention relates to a wiring member, a metal component with resin, and a resin-sealed semiconductor device, as well as to manufacturing methods for the metal component with resin and the resin-sealed semiconductor device, and in particular to technology for improving the adhesion between metal and resin.

BACKGROUND ART

Resin is widely used in semiconductor devices and wiring members.

Generally speaking, semiconductor devices such as integrated circuits (IC), large-scale integrated circuits (LSI) and the like are manufactured by connecting the semiconductor element to the leads through wire bonding or similar, fixing resin thereto in such a manner that a portion of the leads remains exposed, and packaging the whole through resin sealing.

FIGS. 15A through D are schematic cross-section diagrams showing the manufacturing processing for a resin-sealed QFP (Quad Flat Package) semiconductor device.

First, the semiconductor chip 94 is mounted onto the die-pad 93b of the leads 93 (die-pads 93a and 93b). The semiconductor chip 94 is then connected to the die-pads 93a and 93b via a wire 95.

Afterward, the leads 93 are loaded onto the fixed mold 92 (see FIG. 15A).

Next, the movable mold 91 is pressed onto the fixed mold 92 so as to close and form an inner space (cavity 97) within the two molds 91 and 92. Then, thermosetting resin is injection-molded into the cavity 97 via the gate 96 in the movable mold 91 so as to resin-seal the semiconductor chip 94 and so on (see FIG. 15B).

After the thermosetting resin has hardened and formed the molded resin 98, the two molds 91 and 92 are opened and the resin-molded product 9z is pushed out using a non-diagrammed ejector pin. Then, the outer leads 931a of the resin-molded product 9z are bent, thus completing the semiconductor device 9 (see FIG. 15D).

When the semiconductor device 9 is mounted, the outer leads 931a are connected to the substrate 99 via solder 90 (see FIG. 15D).

The above-described manufacturing method for a QFP semiconductor device exists in forms other than the example here given, such as that used for light-emitting diode (LED) devices. There, for example, a light-emitting diode element is loaded and connected to leads inside a mortar-shaped reflector using a substrate formed in such a manner that a portion of the leads is exposed. Afterward, transparent sealing resin fills in the reflector to complete manufacturing. Currently, silicone resin is widely used as the sealing resin given the better light transmittance thereof relative to epoxy resin.

Furthermore, resin is used as the insulating film and solder resist layer in film carrier tape used for mounting of electronic components in IC, LSI, and the like, such as TAB (Tape Automated Bonding) tape, T-BGA (Tape Ball Grid Array) tape, ASIC (Application Specific Integrated Circuit) tape, and so on. Such tape comprises an insulating film made of polyimides or similar, a wiring pattern layer made of Cu, and a solder resist layer, layered in that order.

CITATION LIST

Patent Literature

[Patent Literature 1]
  Japanese Patent Application Publication No. H07-254622
[Patent Literature 2]
  Japanese Patent Application Publication No. H10-329461
[Patent Literature 3]
  Japanese Patent Application Publication No. 2002-33345
[Patent Literature 4]
  Japanese Patent Application Publication No. 2001-144145

SUMMARY OF INVENTION

Technical Problem

However, the following problems arise in using resin-molded products as semiconductor devices, LED devices, and film carrier tape.

The first problem is that, when sealing resin is injection-molded, the resin adheres to additional regions of the leads not expected to be resin-sealed. As shown in expansion P of FIG. 15B, which shows the semiconductor device processing, owing to resin injection at a fixed pressure, thin resin film (known as resin burrs) 98a may form at the surfaces of the outer leads 931a of the leads 93 by resin flowing into gaps 900 of the mold (FIG. 15C). Such gaps 900 emerge from imprecisions in the molds 91 and 92. The injection-time pressure causes external overflow through such gaps 900, which in turn causes the formation of resin burrs 98a as the resin flows out. If resin burrs 98a form, then further problems arise with respect to the joining strength and the electrical connectivity between the outer leads 931a and the substrate 99b in subsequent processing. Preventive measures involve high-precision methods between the molds 91 and 92, but not only is the cost of setting the molds in such a manner prohibitive, but the mechanical precision required to completely prevent the formation of gaps is extremely difficult to achieve. Accordingly, in practice, resin burr formation cannot be prevented. As such, before joining processing onto a substrate, elimination processing is required to eliminate the resin burrs 98a. As such, manufacturing efficiency is diminished and manufacturing costs increase problematically.

Patent Literature 1 through 3 suggest measures for preventing the formation of gaps between molds. However, the technology disclosed in Patent Literature 1 and 2 is technology for strengthening the pressure exerted on the leads by the mold, which may in turn cause deformations due to excess stresses therein or otherwise cause damage to the molds or leads. Also, Patent Literature 3 describes technology for tightly sealing the gap-forming portions of the molds by preemptively applying tape thereto. However, at relatively high temperatures, peeling and damage to such tape may, if used, arise due to mechanical friction involved in the injection molding processing. Furthermore, applying such tape adds the problems of reduced manufacturing efficiency paired with increased costs.

In addition to the above, there is a problem in that the adhesion between the leads and the sealing resin is insufficient. FIGS. 16A and 16B are cross-sectional diagrams schematically describing this problem. Generally speaking, sealing resin (molded resin 98) is influenced by environmental humidity, and water infiltration therein is likely. Given insufficient adhesion between the leads 93a and 93b and the sealing resin (molded resin 98), slight gaps form at the interface between the two (see FIG. 16A).

Water infiltrates these gaps and gradually accumulates therein. When the semiconductor device 9 is mounted onto the substrate 99, the water so accumulated is vaporized by the reflow heat of the solder 90 and sudden volumetric expansion occurs in the above-described gap portions. As a result, peeling may arise therein and cracks may form in the molded resin 98 (see FIG. 16B). If such peeling or cracking occurs, additional water and further impurities may infiltrate the semiconductor device 9, in turn leading to circuit breaks and short-circuits in the semiconductor chip 94 and damaging the reliability of the seal. Also, the accumulation of water in the gaps gradually causes short-circuiting in the semiconductor chip 94, which may cause malfunctions.

A second problem occurs in LED devices, in which an LED chip is sealed using silicone as the sealing resin. While silicone resin ensures high transparency, the linear expansion coefficient thereof is greater than that of epoxy resin. Therefore, when the silicone resin is used for injection molding processing onto a substrate, thermal changes (so-called thermal history) occur in that the silicone resin thermally contracts. As such, peeling may occur between the silicone resin and the leads, and inadequate contact therebetween may degrade product capabilities or cause insufficient joining strength.

In addition, if high-transparency addition polymerizing silicone resin is used, then due to the presence of Pt catalysts required for addition polymerization, discoloration may occur in the Ag plating, thus reducing the reflective efficacy thereof. Furthermore, given that silicone resin is highly permeable to gasses, corrosive gasses may penetrate the silicone resin, coming into contact with the Ag plating and causing discoloration thereof.

A third problem occurs for LED devices in relation to Ag plating applied to the leads to enhance the luminescent efficacy thereof. While Ag is known for high reflective efficacy with respect to long-wavelength visible light, the reflective efficacy thereof with respect to short-wavelength light (≤500 nm) is low. Accordingly, if a diode producing blue, violet, or ultra-violet light is mounted on the LED device, the reflective efficacy thereof may be insufficient.

Also, if Ag plating is applied to the reflector of an LED device with a reflector formed so as to surround the LED chip, unwanted gases present during manufacturing may adhere to the surface of the Ag plating and cause degradation therein. Accordingly, the expected reflective efficacy of the Ag plating is diminished, thus decreasing the luminescent efficacy of the LED device.

Additionally, if thermoplastic resin or the like is used for the reflector, then outgassing inherent therein may adhere to the leads, which may cause wire bonding defects. That is, the intervention of outgassing may diminish the joining strength between the leads and the wire, leading to wire non-adhesion, which is a problem that occurs when bonding fails or the wire is removed.

A fourth problem occurs in film carrier tape, when Sn plating is used for the wire pattern layer.

The surface of the wire pattern layer is connected to mounted components by solder. For this reason, Sn plating is preemptively applied thereto. In the plating processing, the end portions of the solder resist layer may curl up due to atmospheric heat. A problem arises in that a local electric cell may form between the curled-up solder resist layer and the surface of the wire pattern layer, as well as between other parts of the wire pattern layer and surface regions, due to the differing ionization tendencies of Sn ions and Cu ions (see FIG. 17A). If a local electric cell forms, an erosion region then forms due to the dissolution of Cu ions out of the surface of the wire pattern layer. Therefore, the mechanical strength of the film carrier tape is decreased after Sn plating, and uniform plating cannot be achieved.

As described above, unsolved problems remain in connection to the use of resin for semiconductor devices, film carrier tape, and the like.

The present invention has been achieved in consideration of the above problems, and as such, a first aim thereof is to prevent resin burr formation and to constrain peeling and cracking between the leads and the resin. Thus, the present invention provides a semiconductor device and a manufacturing method therefor with good electrical connectivity and joining strength as well as sealing reliability.

A second aim is to improve the adhesion between the silicone resin and the leads while constraining the problems of degradation or discoloration of structural elements, luminescent efficacy deterioration, and wire non-adhesion. Thus, the present invention also provides an LED device able to produce good luminescent characteristics.

A third aim is to enable sufficient reflectivity for relatively short-wavelength light. Thus, the present invention also provides an LED device able to produce superb luminescent efficacy.

A fourth aim is to preserve manufacturing efficacy while avoiding damage to the wire pattern layer at Sn plating processing time. Thus, the present invention also provides a film carrier tape able to produce a superb Sn plating layer with great mechanical strength and adhesion.

Solution to Problem

In order to solve the above problems, the present invention provides an organic compound forming a self-assembling film by aligning an extremity of a principal chain on a metal surface, wherein the principal chain comprises the following.

The principal chain comprises one or more chains selected from the group consisting of a methylene chain, a fluoromethylene chain, a siloxane chain, and a glycol chain; and one or more skeletons selected from the group consisting of an aromatic imide skeleton and an amide skeleton.

Alternatively, the principal chain comprises a N-containing heterocycle containing two or more N atoms. The N-containing heterocycle comprises one or more compounds selected from the group consisting of imidazole, triazole, tetrazole, oxydiazole, thiadiazole, pyrimidine, pyridazine, pyridine, and triazine.

Also, the principal chain further comprises one or more skeletons selected from the group consisting of an aryl skeleton, an acene skeleton, a pyrene skeleton, a phenanthrene skeleton, and a fluorene skeleton.

The principal chain further comprises, farther from the extremity thereof than the N-containing heterocycle, one or more skeletons selected from the group consisting of an aryl skeleton, an acene skeleton, a pyrene skeleton, a phenanthrene skeleton, and a fluorene skeleton.

Preferably, in the above-described organic compound, the principal chain has, at the extremity thereof, a first functional group able to bond with metals, and the principal chain has, at another extremity thereof, a second functional group possessing predetermined properties.

Also, the first functional group preferably comprises one or more compounds selected from the group consisting of a thiol compound, a sulfide compound, and a N-containing heterocyclic compound.

In addition, the present invention provides a manufacturing method for a metal component with resin, comprising an organic film formation step of (a) adhering a material that includes functional organic molecules, each comprising (i) at an extremity of a principal chain, a first functional group able to bond with metals, and (ii) at another extremity of the principal chain, a second functional group possessing predetermined properties, to leads composed of metal, (b) causing the first functional groups to bond with metal atoms that compose the leads, and (c) forming an organic film through self-assembly by the functional organic molecules; and a resin adhesion step of, after the organic film formation step, affixing resin to predetermined surface regions of the leads on which the organic film is disposed, wherein the above-described organic compound is used in the organic film formation step.

In the above-described manufacturing method, the resin used in the resin adhesion step is a thermosetting resin. The thermosetting resin used in the resin adhesion step comprises one or more resins selected from the group consisting of epoxy resin, phenol resin, acrylic resin, melamine resin, urea-formaldehyde resin, unsaturated polyester resin, alkyd resin, polyimide resin, polyamide resin, and polyether resin, and each of the second functional groups comprise one or more members selected from the group consisting of a hydroxyl radical, carboxylic acid, acid anhydride, primary amine, secondary amine, tertiary amine, amide, thiol, sulfide, imide, hydrazide, imidazole, diazabicycloalkene, organic phosphine, and a triphenylboron amine complex.

In the above-described manufacturing method, the organic film formed in the organic film formation step is formed in regions extending over a greater area than the predetermined surface regions of the leads where the resin is to adhere in the resin adhesion step.

When the thermosetting resin used in the resin adhesion step is silicone resin (including silicone resin that includes one or more groups selected from the group consisting of epoxy groups and alkoxysilyl groups), each of the second functional groups preferably comprise one or more members selected from the group consisting of a vinyl group, organic hydrosilane, a hydroxyl radical, acid anhydride, primary amine, and secondary amine.

When the thermosetting resin used in the resin adhesion step is silicone resin (including silicone resin that includes one or more groups selected from the group consisting of epoxy groups and alkoxysilyl groups), each of the second functional groups preferably comprise a metal complex containing one or more metals selected from the group consisting of Pt, Pd, Ru, and Rh.

Also, each of the second functional groups may preferably comprise one or more compounds selected from the group consisting of a fluorescent compound and a phosphorescent compound.

The organic film formation step preferably comprises a dispersion fluid preparation sub-step of preparing an organic molecule dispersion fluid by dispersing the functional organic molecules in a solvent; and an immersion sub-step of immersing portions of the leads that include the regions extending over a greater area than the predetermined surface regions of the leads where the resin is to adhere in the organic molecule dispersion fluid.

A manufacturing method for a semiconductor device pertaining to the present invention that includes the above-described manufacturing method further comprises a connection step between the organic film formation step and the resin adhesion step in which the leads are electrically connected to a semiconductor element; wherein during the resin adhesion step, the resin is molded in such a manner that the semiconductor element is enclosed thereby while portions of the leads remain exposed.

Also, according to the present invention, for a wiring member with metal leads having an organic film that is formed through self-assembly by an organic compound and that adheres to surfaces thereof, the organic compound has a structure such that the following (i) and (ii) are each arranged therein: (i) at an extremity of a principal chain, a first functional group that imparts bonding capability by which formation of any among metallic bonds, hydrogen bonds, and coordinate bonds via metal compounds, is made possible with respect to the leads, and (ii) at another extremity of the principal chain, a second functional group that causes or enhances resin hardening, the principal chain of the organic compound comprises the following.

The principal chain of the organic compound comprises one or more chains selected from the group consisting of a methylene chain, a fluoromethylene chain, a siloxane chain, and a glycol chain; and one or more polar groups selected from the group consisting of hydroxyl radicals, ketone, thioketone, primary amine, secondary amine, and aromatic compounds.

The principal chain of the organic compound comprises one or more chains selected from the group consisting of a methylene chain, a fluoromethylene chain, a siloxane chain, and a glycol chain; and one or more skeletons selected from the group consisting of an aromatic imide skeleton and an amide skeleton.

the principal chain of the organic compound comprises a N-containing heterocycle containing two or more N atoms. The N-containing heterocycle comprises one or more compounds selected from the group consisting of imidazole, triazole, tetrazole, oxydiazole, thiadiazole, pyrimidine, pyridazine, pyridine, and triazine.

The principal chain of the organic compound further comprises one or more skeletons selected from the group consisting of an aryl skeleton, an acene skeleton, a pyrene skeleton, a phenanthrene skeleton, and a fluorene skeleton.

Also, for a metal component with resin pertaining to the present invention where resin is affixed to a portion of the above-described wiring member, wherein the organic film adheres to and is formed over a greater area than the surface area of the wiring unit where the resin is affixed.

Additionally, with respect to the above-described wiring member, a reflector which possesses a mortar-shaped surface and on which an LED chip is mounted is arranged, a plating layer made of Ag is formed over the surface of the reflector, the organic film further adheres to the surface of the plating layer, and the first functional group of the organic compound bonds with the plating layer.

For an LED device pertaining to the present invention, an LED chip is arranged in a reflector of the above-described metal component with resin, and transparent resin fills the reflector surface.

With respect to the wiring member, a reflector which possesses a mortar-shaped surface and on which an LED chip is mounted is arranged, and the reflector is composed of thermoplastic resin.

An LED chip is arranged in a reflector of the above-described metal component with resin, and transparent resin fills the reflector surface. The transparent resin is intermixed with a hydrophilic additive.

With respect to the wiring member pertaining to the present invention, a semiconductor element is electrically connected onto the leads, the wiring member is partially exposed, and the semiconductor element is resin-sealed within a region in which the organic film is formed.

Advantageous Effects of Invention

Given the above structure, the present invention is able to produce various advantageous chemical effects between leads or similar made out of metal and resins adhering thereto by forming a self-assembling film of functional organic molecules at the surface of the leads and to solve the problems inherent in conventional technologies.

That is, by using functional organic molecules where a first functional group imparting the ability to bond with metals is arranged at one end of a principal chain, an organic film can be formed through self-assembly of the functional organic molecules oriented such that a second functional group faces the top surface of the leads. Accordingly, if the second functional group causes or enhances hardening in thermosetting resins, then the bonding strength of the resin adhering to the film will be enhanced, and the resin will also harden sooner.

As a result, even if gaps are present in the molds used at injection-molding time, resin can be prevented from leaking into such gaps because the resin that fills the cavity hardens sooner upon contact with the organic film. Accordingly, the post-resin-molding resin burr removal step is rendered unnecessary.

Also, according to the present invention, the above-described advantageous effects can be realized solely through the use of the organic film. As such, there is no need to alter existing injection-molding devices nor to add new devices. Therefore, a low-cost and high-efficiency manufacturing process for semiconductor devices with good electric conductivity can be realized.

In addition, through the use of the above-described functional organic molecules, a semiconductor device can be realized with enhanced adhesion between the sealing resin (molded resin) and the leads by interposing the organic film therebetween, thus effectively preventing the formation of gaps at the interface thereof. Accordingly, even if atmospheric water penetrates the semiconductor device through the sealing resin (molded resin), the problems present in conventional technology in which such water accumulates between the sealing resin (molded resin) and leads causing cracks or peeling at semiconductor device reflow time, which in turn cause short-circuiting in the semiconductor chip as water infiltrates the cracks, can be avoided.

Furthermore, through the use of a structure such that the principal chain of the functional organic molecules is made up of one or more chains selected from the group consisting of a methylene chain, a fluoromethylene chain, a siloxane chain, and a glycol chain and contains one or more polar groups selected from the group consisting of hydroxyl radicals, ketone, thioketone, primary amine, secondary amine, tertiary amine, ether, thioether, and aromatic compounds, or else such that the principal chain of the functional organic molecules is made up of one or more chains selected from the group consisting of a methylene chain, a fluoromethylene chain, a siloxane chain, and a glycol chain and contains one or more skeletons selected from the group consisting of an aromatic imide skeleton and an amide skeleton, the present invention brings about stronger mutual bonds (the effect of stacking due to hydrogen bonds or London dispersion) between the principal chains of neighboring functional organic molecules, and is thus able to strengthen the organic film itself and enhance the thermal resistance thereof.

In particular, if the structure is such that the principal chains of the functional organic molecules comprise a N-containing heterocycle containing two or more N atoms, then given the heightened melting point and superb stacking effects imparted to the organic film thereby, the anchor effects at work at the surface of the metal leads prevent metal re-crystallization and ensure a stable organic film, even at high temperatures.

Also, if the structure is such that the principal chains of the functional organic molecules comprise one or more skeletons selected from the group consisting of an aryl skeleton, an acene skeleton, a pyrene skeleton, a phenanthrene skeleton, and a fluorene skeleton, then UV protection effects are at work in the film, preventing discoloration at the metal surface. In particular, these effects prevent blackening in the metal surface of Ag plating.

Also, if one or more members selected from the group consisting of vinyl, organic hydrosilane, a hydroxyl radical, acid anhydride, primary amine, and secondary amine is used as the second functional group, then strong chemical bonding can be achieved between the organic film and the resin, the resin being silicone resin or else a silicone resin that includes one or more groups selected from the group consisting of epoxy groups and alkoxysilyl groups.

Accordingly, by applying an organic film made up of the functional organic molecules to the leads of an LED device, peeling, cracking, and the like can be prevented from occurring between the silicone resin and the leads, high-temperature contact degradation and inadequate joining strength or similar can be constrained, making possible the realization of an LED device with stable luminescent efficacy. Also, given the minute coordination between principal chains of the organic film, Pt catalysts and corrosive gasses needed for addition polymerization of the silicone resin can be prevented from causing discoloration in the Ag.

Furthermore, if the second functional group of the functional organic molecules forming the organic film applied to the leads of an LED device comprises a Pt complex, then silicone resin used for filling hardens extremely fast. Accordingly, the silicone resin can effectively be prevented from flowing into gaps between the reflector and leads, despite the presence of such unwanted gaps at the border. The silicone resin may also be a silicone resin-including electrically conductive paste (such as Ag paste or similar die-bonding material). By using silicone resin-including electrically conductive paste for die-bonding, the semiconductor chip and die-pads of the LED device or similar can be joined more strongly. Given the relative lack of degradation therein in comparison to conventional epoxy resin-including electrically conductive paste, more stable electrical and thermal conductivity can be realized.

Additionally, if the second functional group of the functional organic molecules forming the organic film applied to the leads of an LED device comprises a fluorescent compound or a phosphorescent compound, then the reflective efficacy with respect to short-wavelength visible light or UV light can be enhanced, even if Ag plating or the like, which has poor reflective efficacy with respect to such light, is used. Thus, the reflective efficacy of the device as a whole can be relied upon.

If Ag plating is formed over a reflector arranged so as to surround an LED chip and an organic film composed of the functional organic molecules of the present invention is formed over the Ag plating through self-assembly thereof, then unwanted gasses present in the manufacturing processing (such as those outgassed by the thermoplastic resin of the reflector) can be prevented from coming into direct contact with the Ag plating. As a result, degradation of the Ag due to such gasses and damage to the reflective properties of the plating can be avoided, making possible the manufacture of an LED device with better reflective efficacy.

Also, by forming the organic film of the present invention over the leads, outgassing from the thermoplastic resin or similar used for the reflector can be prevented from coming into direct contact therewith. As a result, the problem of wire non-adhesion in the leads due to the presence of such outgassing can be prevented, making possible significantly more reliable wire bonding.

In addition, for a film carrier tape, if an organic film is formed of functional organic molecules with a first functional group that imparts metal bonding characteristics to a wire pattern layer and a second functional group that forms bonds with a solder resist layer, then enhanced stability can be obtained for the layer structure of the wire pattern and solder resist layers.

Accordingly, the ends of the solder resist layer can be prevented from curling up away from the wire pattern during the Sn plating processing at manufacturing time. As such, the formation of a local electric cell can be suppressed, enabling higher-quality film carrier tape manufacture.

Furthermore, if the principal chain that makes up the greatest portion of the functional organic molecules is made up of hydrophobic hydrocarbons or fluorocarbons, then a water resistance effect is at work in the wiring pattern layer to which the organic film has been applied. Thus, migration can be effectively suppressed and the stability thereof as a conductive product can be preserved.

The organic film made up of the functional organic molecules pertaining to the present invention is of monomolecular-level thickness, yet is effective in preventing corrosion and rust in the area of the leads to which the film is applied and also enhances the resistance thereof. Furthermore, there is no need to remove the organic film after arrangement. The functionality and structure thereof is completely different from general surface processing agents, surfactants, dyes, and so on.

BRIEF DESCRIPTION OF FIGURES

FIGS. 5A and 5B describe the effects of constraining metal re-crystallization through a film of functional organic molecules.

DESCRIPTION OF EMBODIMENTS

The Embodiments of the present invention are described below with reference to the figures.

Naturally, the present invention is not limited to the following Embodiments, but may also be realized as variations thereof provided that such variations do not deviate from the technical field at hand.

[Embodiment 1]

1. Configuration of the Semiconductor Device

Figure 1A:
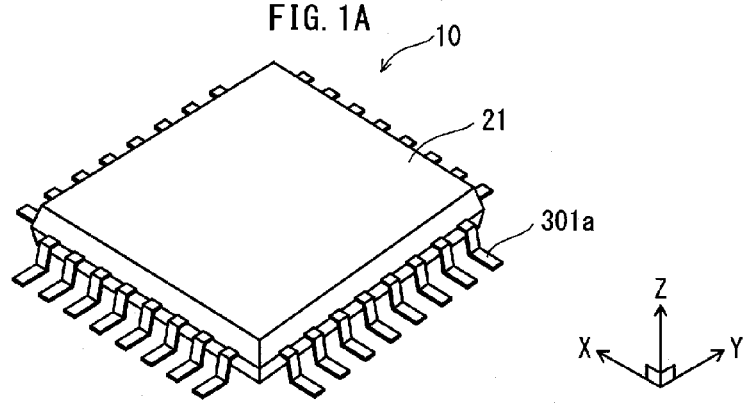
FIGS. 1A through 1C show the configuration of the semiconductor device pertaining to Embodiment 1.
Figure 1B:
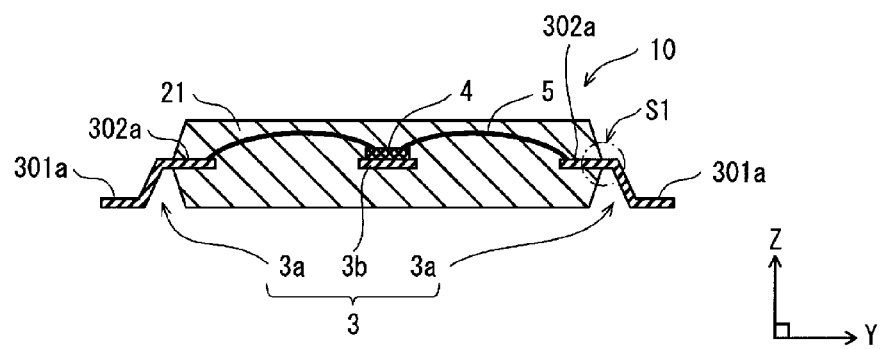
Figure 1C:
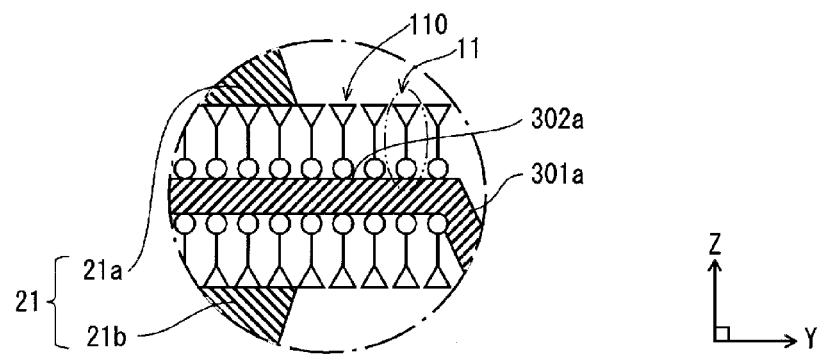

FIG. 1A is an outside perspective view showing the configuration of the semiconductor device (QFP: Quad Flat Package 10) used as an applicable example of the present invention. FIG. 1B is a cross-sectional diagram along the yz plane of the QFP 10. FIG. 1C is an expanded view of the S1 portion of the QFP 10 shown in FIG. 1B.

The QFP 10 is a surface-mounted semiconductor device that uses IC, LSI, or similar integration. The QFP 10 comprises a semiconductor chip 4, leads 3, a wire 5, molded resin 21, and the like.

The leads 3 are punched from a plate composed of a metal with great electrical conductivity (in this example, a copper alloy), and manufactured into a combination of die-pads 3$a$ and 3$b$.

Being a surface-mounted semiconductor device, the QFP 10 comprises, as shown in FIG. 1A, molded resin 21 formed as a flat plate of uniform thickness as well as outer leads 301a that extend from the perimeter thereof as a subset of the die-pads 3a.

As shown in FIG. 1B, the molded resin 21 incorporates therein the die-pads 3a and the semiconductor chip 4 mounted in a structure such that the die-pads 3a and 3b are connected via the wire 5 and non-diagrammed electrode pads. The die-pad 3b is joined to the semiconductor chip 4 by a non-diagrammed conductive paste, such as a silver paste.

The die-pads 3a are made up of the inner leads 302a in areas sealed within the molded resin 21 and of the outer leads 301a in areas exposed to ambient air. The cross-section of the outer leads 301a illustrates the S-curve shape thereof.

The QFP 10 is characterized in that, at the border regions of the inner leads 302a and the outer leads 301a of the die-pads 3a and 3b in the QFP 10 (portion S1 of FIG. 1B), the surface features an organic film 110 formed thereon through self-assembly of functional organic molecules.

The details of the organic film 110 are explained below.

2. Configuration of the Organic Film 110

Figure 2A:
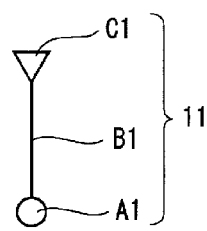
FIGS. 2A and 2B schematically show the configuration of the functional organic molecules pertaining to Embodiment 1.

FIG. 2A is a schematic structural diagram of a single functional organic molecule 11. As shown, one functional organic molecule 11 is made up of a first functional group A1, a principal chain B1, and a second functional group C1, bound together in that order.

The principal chain B1 consists of a glycol chain, a methylene chain, a fluoromethylene chain, a siloxane chain, or similar.

The first functional group A1 is a functional group composed of a compound, chemical structure, or derivative thereof containing one or more member able to cause bonding with metals.

The second functional group C1 is a functional group composed of a compound, chemical structure, or derivative thereof containing one or more member able to cause or to accelerate hardening in thermosetting resins.

As shown in FIG. 1C, each of the functional organic molecules 11 forms a coordinate bond with the surface of the metal die-pad 3a at the first functional group A1 and is oriented so that the second functional group C1, at the opposite end of the principal chain B1, faces the exterior surface. Accordingly, the chemical properties (mutual affinity) emergent from such molecular orientation are such that a monomolecular film (the organic film 110) is the naturally-resulting self-assembled chemical structure. The thickness of the organic film 110 is dependent on the size of the functional organic molecules 11 and is on the order of a few nanometers (see FIG. 1C).

Thus, the organic film 110 is able to minutely protect the surface of the die-pads 3a given the monomolecular-level size thereof. As a result, the surface is protected from corrosion due to gaseous oxygen and water build-up, which in turn is highly beneficial in preventing substitution of noble metal salts.

Considering that, in the QFP 10, the outer leads 301a must be electrically connected to the semiconductor chip 4 through wire bonding, die bonding, or the like, good electrical conductivity must be preserved and, in some cases, metal plating or a similar film must be formed in at least the contact region between the die-pads and the leads 3. In such cases, a metal plating process is necessary. However, the problem posed by dissolution of metal components of the die-pad 3a into the plating liquid due to the ionization tendencies thereof can be advantageously controlled by providing the organic film 110 on the surface of the die-pads 3a in the absence of such metal plating.

The general formula of the functional organic molecules 11 is expressed as A1-B1-C1. The number of carbons forming the principal chain B1 ideally ranges from 4 to 40 carbons. If the number of carbons in the chain is too few, then the principal chain B1 is too short, and thus when the first functional group A1 adheres to the leads 3a, the inter-molecular hydrophobic affinity between the above-described functional organic molecules 11 is weakened due to the hydrophoby of the principal chain B1, and so the outward orientation of the second functional group C1 is more easily lost. On the other hand, if the number of carbons in the chain is too great, then the principal chain B1 is too long, and thus the leads 3a are more easily damaged by soldering, wire bonding, and die bonding.

It should be noted that the principal chain B1 may also have side chains bound thereto.

The details of a chemical structure that can provide the functional organic molecules 11 pertaining to Embodiment 1 of the present invention are explained below.

(First Functional Group A1)

As described above, the first functional group A1 is required to display the characteristics of affinity with metals and of metal bonding (including coordinate bonding). The first functional group A1 may be composed of any compound, chemical structure, or derivative thereof containing one or more member displaying such characteristics.

For example, thiol or a thiol compound that includes same, a sulfide compound (such as a disulfide compound), a N-containing heterocyclic compound (such as an azole or azine compound), or else any compound, chemical structure, or derivative thereof that includes one or more of the above may be used, ideally with hydrogen bonding or coordinate bonding characteristics with respect to metal atoms.

If the first functional group A1 is a thiol group (R—SH, where R may be any alkane, alkene, or similar functional group), then the group will coordinate with metal atoms that can be polyvalent cations, such as Au or Ag, to form Au—S—R or Ag—S—R covalent bonds. Thus, the functional organic molecules 11 adhere to the die-pads 3a. Similarly, if the first functional group A1 is a disulfide group (R1-S—R2), then the group will form Au(—S—R1) (—S—R2) or Ag(—S—R1) (—S—R2) covalent bonds, resulting in a strong bond structure.

If the first functional group A1 contains an azole or azine compound, then the lone pairs of the N atoms within the molecules that form such a compound are able to form coordinate bonds with metals than can be polyvalent cations. For instance, imidazole compounds, triazole compounds, and triazine compounds are all ideal given the ease with which such compounds can form coordinate bonds with metals, mainly with Cu.

Depending on which of the above varieties are used, covalent bonds, coordinate bonds, or even hydrogen bonds may simultaneously form. However, such multi-various bonding can be expected to result in a stronger bond structure.

(Principal Chain B1)

The principal chain B1 is, generally speaking, a chain of methylene-like organic molecules (i.e. a chemical compound, structure, or derivative that includes one or more members selected from a methylene chain, a fluoromethylene chain, a siloxane chain, and a glycol chain). A methylene chain is ideal given the inter-molecular associations therein and the ability thereof to form minute carbon chains at the supra-molecular hydrocarbon level. Furthermore, the inventors have ascertained that use of a methylene chain results in comparatively faster formation of the organic film.

If the principal chain B1 uses a fluoromethylene chain, then due to the stronger hydrophoby thereof in comparison to a methylene chain, the organic film will, once formed, have a stronger ability to suppress water penetration between the leads 3 and the film itself. As a result, better bonding is preserved between the organic film and the leads, which is ideal in that the organic film is thus made less likely to peel away due to thermal history.

If the principal chain B1 uses a siloxane chain, then an organic film with superb heat and weather resistance characteristics will result. Therefore, results can be achieved in preventing alteration or damage to the organic film itself even if exposed to a relatively high-temperature environment, such as that which occurs during semiconductor mounting processes.

If the principal chain B1 uses a glycol chain, then the chain can be made to dissolve simply in water and other polar solvents, which is useful for film formation.

Accordingly, the principal chain B1 preferably has a structure that uses a glycol chain, or else that uses a combination of a glycol chain and one or more members selected from the group consisting of a methylene chain, a fluoromethylene chain, and a siloxane chain.

Also, if the heat conditions for wire bonding or the like are set to relatively high temperatures, then further improvements are desirable with respect to the heat resistance of the organic film 110 that uses the functional organic molecules 11. In such a case, the principal chain B1 should preferably use a polar group that includes one or more members selected from the group consisting of a hydroxyl radical, a ketone, a thioketone, a primary amine, a secondary amine, a tertiary amine, an ethyl, a sulfide, and an aromatic compound.

In particular, use of an amide group (composed of a ketone and a secondary amine), an aromatic amide, or an aromatic imide group (composed of a ketone, a tertiary amine, and an aromatic ring), or else of a combination of the above as the polar group is preferable.

Use of a principal chain B1 that includes such a polar group brings about stronger mutual bonds (the effect of stacking due to hydrogen bonds or London dispersion) between the principal chains B1 of neighboring functional organic molecules 11 in the organic film 110. The organic film 110 is thus made stronger. In other words, as the organic film 110 remains stable even in a high-temperature environment, the heat resistance thereof is enhanced.

(Second Functional Group C1)

The second functional group C1 is required to cause or to enhance hardening in thermosetting resin. Any structure that includes a chemical compound, structure, or derivative thereof containing one or more member exhibiting such characteristics may be used.

For instance, the second functional group C1 may use any chemical compound, structure, or derivative thereof that includes one or more members selected from the group consisting of a compound with a hydroxyl radical, a compound with a carboxylic acid, a compound with an acid anhydride, a compound with a primary amine, a compound with a secondary amine, a compound with a tertiary amine, a compound with a quaternary ammonium salt, a compound with an amide group, a compound with an imide group, a compound with a hydrazide group, a compound with an imine group, a compound with an amidine group, a compound with imidazole, a compound with triazole, a compound with tetrazole, a compound with a thiol group, a compound with a sulfide group, a compound with a disulfide group, a compound with diazabicycloalkene, a compound with organic phosphine, a compound with an organic phosphine compound triphenylboron amine complex, or a compound similar to the above examples. Use of such a compound or derivative thereof results in an instantaneous hardening reaction upon contact with thermosetting resin, thus enabling the second functional group C1 to bond with such resin.

If the second functional group C1 is phthalic anhydride, itself an acid anhydride, then the group can be used as a hardening agent for epoxy resin due to the bonds formed by ring-opening polymerization with the epoxy group found therein.

Figure 2B:
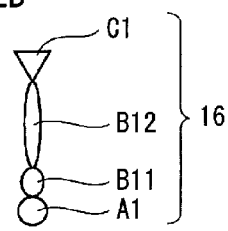

Aside from the functional organic molecules 11, functional organic molecules 16, shown in FIG. 2B, can also be used.

As shown, one of the functional organic molecules 16 is composed of the first functional group A1, a principal chain B11, a principal chain B12, and the second functional group C1, bound together in that order.

Further, the principal chain B11 includes one or more varieties of a N-containing heterocyclic compound containing two or more N atoms (i.e. imidazole, triazole, tetrazole, oxadiazole, thiadiazole, pyrimidine, pyridazine, pyridine, triazine, or a derivative of the above). The principal chain B12 includes one or more varieties of an aryl skeleton (i.e. phenyl, biphenyl, terphenyl, quaterphenyl, quinquaphenyl, or sexiphenyl), an acene skeleton (i.e. naphthalene, anthracene, naphthacene, or pentacene), a pyrene skeleton, a phenanthrene skeleton, a fluorene skeleton, or a derivative of the above.

The first functional group A1 and the second functional group C1 are as explained above for the functional organic molecules 11.

In each the functional organic molecules 16, much like the functional organic molecules 11, the first functional group A1 also forms coordinate bonds with the metal surfaces of the die-pads 3a, and thus, the functional group C1, at the opposite end of the principal chains B11 and B12, is oriented to face the exterior surface. Thus an organic film (monomolecular film) is formed as a self-assembled chemical structure and minutely protects the surfaces of the die-pads 3a.

The structure of the functional organic molecules 16 is expressed as A1-B11 (a N-containing heterocyclic compound containing two or more N atoms, or a derivative thereof)—B12 (an aryl skeleton, an acene skeleton, a pyrene skeleton, a phenanthrene skeleton, a fluorene skeleton, or a compound or derivative thereof made up of one or more varieties of the above)—C1.

Ideally, the number of aromatic rings included in the principal chain B12 should be one to ten aromatic rings, and most ideally two to six rings. If the number of aromatic rings in the principal chain B12 is too few, then the principal chain B12 is too short, and thus when the first functional group A1 adheres to the leads 3a, the inter-molecular hydrophobic affinity between the above-described functional organic molecules 11 is weakened due to the hydrophoby of the principal chain B12, and the outward orientation of the second functional group C1 is more easily lost. On the other hand, if the number of aromatic rings in the principal chain B12 is too great, then the principal chain B12 is too long, and thus the leads 3a are more easily damaged by soldering and wire bonding.

It should be noted that the principal chains B11 and B12 may also have side chains bound thereto.

Furthermore, a methylene chain, a fluoromethylene chain, a siloxane chain, or a glycol chain may be interposed between the principal chains B11 and B12 or else between the principal chain B12 and the second functional group C1. Accordingly, intra-molecular nuclear rotation is made easier and stronger minute coordination between chains is obtained from the flexibility thereof.

Also, an ether, thioether, ketone, thioketone, secondary amine, tertiary amine, amide, or sulfone may be interposed between the principal chain B11 and the principal chain B12, or between the principal chain B11 and the second functional group C1. Accordingly, intra-molecular nuclear rotation is made easier, and additionally, the minuteness and coordination of the principal chains is improved through hydrogen bond inter-molecular affinity.

The chemical structure of the functional organic molecules 16 is detailed below.

(Principal Chain B11)

The principal chain B11 may use a N-containing heterocyclic organic molecule or the like containing two or more N atoms (i.e. a compound, structure, or derivative thereof containing one or more varieties among imidazole, triazole, tetrazole, thiadiazole, pyrimidine, pyridazine, pyridine, and triazine). The N-containing heterocyclic compound containing two or more N atoms ideally has high heat resistance as a compound and is thereby able to improve the thermostability of the bond between the first functional group A1 and the metal. In addition, the inventors have discerned that, if a five-member cyclic compound such as imidazole, triazole, tetrazole, thiadiazole and so on is used, then when thermal history is added after the formation of the organic film, topmost surface exposure of diffuse metal can be prevented through the formation of a surface complex by diffusion of interior metal toward the surface and the presence of N-atom lone pairs.

If the principal chain B11 uses a six-member cyclic compound such as pyrimidine, pyridazine, pyrazine, triazine and so on, then the chemical structure will be such that the first functional group A1 is able to form two bonds. Thus, the bond power of the first functional group A1 can be made equivalent to twice that of a five-member cyclic compound, which in turn strengthens the bond stability of the organic film itself. As a result, good bonding is preserved between the organic film and the leads, which is ideal in that the organic film is thus made less likely to peel away due to thermal history.

Use of a principal chain B11 as described brings about stronger mutual bonds (the effect of stacking due to hydrogen bonds or London dispersion) between the principal chains B11 of neighboring functional organic molecules 16 in the organic film 110. The organic film 110 is thus made stronger. In other words, the organic film 110 is effectively prevented from dispersing in a high-temperature environment through the aforementioned mutual bonding, and the heat resistance thereof can be rapidly improved.

(Principal Chain B12)

The principal chain B12 may use an aromatic compound that includes one or more members selected from the group consisting of an aryl skeleton (i.e. phenyl, biphenyl, terphenyl, quaterphenyl, quinquaphenyl, or sexiphenyl), an acene skeleton (i.e. naphthalene, anthracene, naphthacene, or pentacene), a pyrene skeleton, a phenanthrene skeleton, a fluorene skeleton, and a chemical compound, structure, or derivative thereof that includes one or more of the above.

If the principal chain B12 uses an aryl skeleton, then as the number of aromatic rings therein increases, the stronger the resulting mutual bonds (the effect of $\pi$-$\pi$ stacking due to London dispersion) between principal chains B12 become, which in turn remarkably enhances the heat stability of the functional molecule as a whole due to the resulting higher melting point.

Also, if the principal chain B12 has an acene skeleton, then as the number of aromatic rings therein increases, the stronger the resulting mutual bonds between principal chains B12 become, more than is the case for an aryl skeleton. As a result, permeability to corrosive gases and water can be greatly diminished. Furthermore, an acene skeleton shifts the light-absorption spectrum toward longer wavelengths through a conjugated system that grows with increases in the number of aromatic rings. Thus, degradation in short-wavelength (UV) light-absorbing metals such as Ag (i.e. blackening due to oxydation) can be suppressed through the light absorption effect (UV protection effect) of the acene skeleton. These effects, produced by an acene skeleton, are also obtained with an aryl skeleton.

Furthermore, with a pyrene skeleton, a phenanthrene skeleton, or a fluorene skeleton, in addition to the mutual aromatic ring bonding effects and the UV protection effects, a strong effect is present in that light energy can be utilized thereby as fluorescence or as phosphorescence.

The presence of a methylene chain between the principal chains B11 and B12 or between the principal chain B11 and the second functional group C1 is ideal given the intermolecular associations therein and ability thereof to form minute carbon chains at the supra-molecular hydrocarbon level. Furthermore, the inventors have ascertained that use of a methylene chain results in comparatively faster formation of the organic film.

The presence of a fluoromethylene chain between the principal chains B11 and B12 or between the principal chain B11 and the second functional group C1 causes the organic film, once formed, to have a stronger ability to suppress water penetration between the leads 3 and the film itself due to the stronger hydrophoby thereof in comparison to a methylene chain. As a result, strong bonding is preserved between the organic film and the leads, which is ideal in that the organic film is thus made less likely to peel away due to thermal history.

The presence of a siloxane chain between the principal chains B11 and B12 or between the principal chain B11 and the second functional group C1 brings about superb heat and weather resistance. Therefore, results can be achieved in preventing alteration or damage to the organic film itself even if exposed to a relatively high-temperature environment, such as that which occurs during semiconductor mounting processes.

If a glycol chain is present between the principal chains B11 and B12 or between the principal chain B11 and the second functional group C1, then the resulting film can be made to dissolve simply in water and other polar solvents and also has strong affinities with hydrophilic groups, both of which are useful traits.

Also, if an ether, thioether, ketone, thioketone, secondary amine, tertiary amine, amide, or sulfone is interposed between the principal chains B11 and B12 or between the principal chain B11 and the second functional group C1, then intra-molecular nuclear rotation is made easier and further improvements can be made to the coordination and minuteness of the principal chains due to the intermolecular affinities of the hydrogen bonds therein.

Also, if a glycol chain is used in the principal chain B1, then the organic film can be formed through hydrophilic mutual affinities and can be made to dissolve simply in water and other polar solvents. Accordingly, use of a glycol chain, or of a combination of a glycol chain and one or more members selected from the group consisting of a methylene chain, a fluoromethylene chain, and a siloxane chain is ideal.

It should be noted that the principal chain B1 of the functional organic molecules 11 and the principal chains B11 and B12 of the functional organic molecules 16 described above are not limited to Embodiment 1 but are also applicable to be used as the principal chains of the functional organic molecules in other below-described Embodiments wherever appropriate.

3. Semiconductor Device Manufacturing Method

Next, the manufacturing method of the QFP 10 of Embodiment 1 is explained.

The QFP 10 is manufactured through organic film formation processing, in which the organic film 110 is made to adhere to predetermined surfaces of the die-pads 3a, followed by resin adhesion processing, in which the die-pads 3a, the semiconductor chip 4, and so on are resin sealed.

(Organic Film Formation Processing)

Figure 3A:
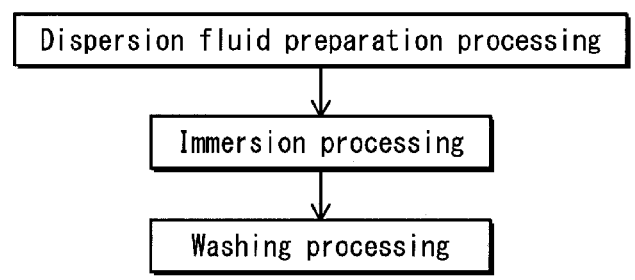
FIGS. 3A through 3B show the formation processing of the organic film pertaining to Embodiment 1.

The organic film formation processing is made up of dispersion fluid preparation sub-processing, film formation sub-processing, and washing sub-processing, in that order (see FIG. 3A).

(Dispersion Fluid Preparation Sub-processing)

The following explanation is given with reference to the organic film 110 using the functional organic molecules 11, yet can be similarly realized by using the functional organic molecules 16.

A dispersion fluid is prepared by dispersing the functional organic molecules 11 in a predetermined solvent. Either water or an organic solvent may be used. If water is used as the solvent, then addition of an anionic, cationic, or nonionic surfactant, as required, is ideal in order to produce dispersal of the functional organic molecules 11. Finally, a boronic, sulfuric acid, or similar pH buffer solution or antioxidant solution may be added in order to stabilize the functional organic molecules 11.

[Film Formation Sub-Processing]

Next, the predetermined surfaces of the die-pads 3a are immersed into a dispersion fluid prepared as described above.

In the dispersion fluid, each of the functional organic molecules 11 is at an energy level that has comparatively high Gibbs energy, and every molecule undergoes random motion (Brownian motion) in the rebound direction due to mutual effects therebetween.

Accordingly, upon immersion of the metal die-pads 3a in the dispersion fluid, the microscopic functional organic molecules 11 bond with the metal of the die-pads 3a through the first functional groups A1 of and thus transition to a steadier state.

Figure 3B:
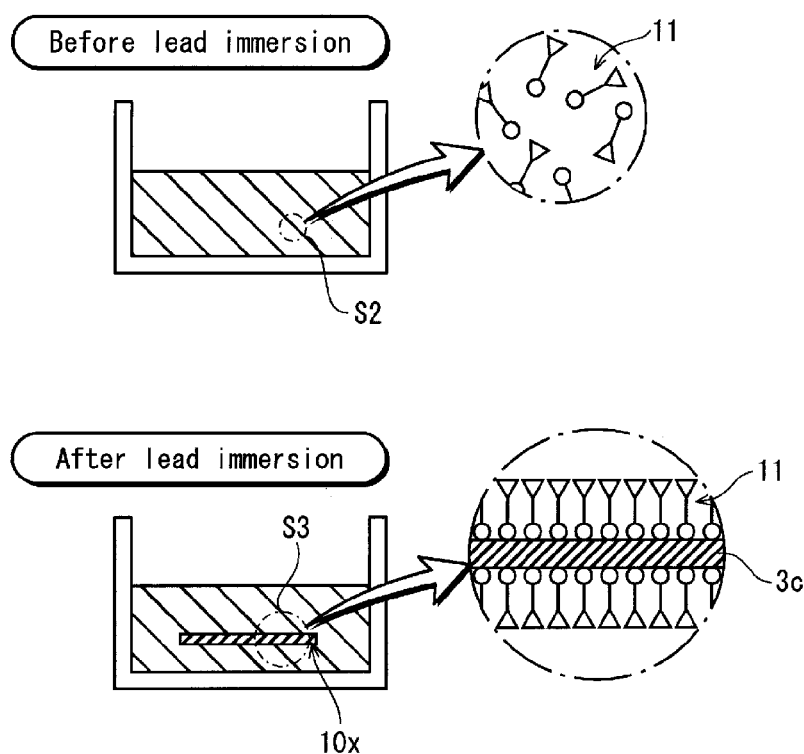

This transition to a steadier state leads, at the macroscopic level, to bond formation by the first functional groups A1 of each of the functional organic molecules with the surface of the die-pads 3a, which in turn leads to mutual stabilization as the principal chains B1 and second functional groups C1 are ordered and aligned, and hence, to the self-assembly of the monomolecular film (see FIG. 3B).

The self-assembling film is formed in accordance with the above principles. Upon removal from the dispersion fluid, the leads 3a acquire a member (hereinafter referred to as wiring member 10x) formed by the organic film 110.

While the above explanation uses the example of FIG. 3B, in which the organic film 110 is formed on the entire surface of the die-pads 3a, it should be noted that a mask pattern with predetermined apertures may be prepared and laid on the leads 3a in advance so that the organic film 110 is formed only on parts of the surface of the leads 3a that correspond to the apertures.

Furthermore, while the above example describes an immersion method using the dispersion fluid, the formation method of the organic film 110 is not limited in this manner and may, for instance, be accomplished through spraying or other methods.

(Washing Sub-Processing)

The above-described wiring member 10x, obtained from the dispersion fluid, must be submitted to washing processing, in which either water or an organic solvent is the washing medium, in order to remove excess functional organic molecules 11 therefrom. Any functional organic molecules 11 in which the first functional group A1 has not directly formed a bond with the metal of the leads 3a must be removed as the advantageous effects of the present invention cannot be obtained therewith. Through the washing sub-processing, any functional organic molecules 11 that have not formed bonds with the die-pads 3a can be simply removed.

This concludes the organic film formation processing.

[Resin Adhesion Processing]

The resin adhesion processing is made up of wiring member mounting sub-processing and resin filling sub-processing, in that order. Each aspect of this sub-processing is explained using the schematic outline diagrams of FIGS. 4A and 4B.

(Wiring Member Mounting Sub-Processing)

First, the semiconductor chip 4 is mounted onto the die-pad 3b using the wiring member 10x produced in the above-described organic film formation processing with the die-pad 3b. Next, the semiconductor chip 4 and the wiring member 10x are connected via the wire 5. Then, the resulting chip-bearing wiring member 10y is mounted onto the fixed mold 2 (see FIG. 4A).

Figure 4A:
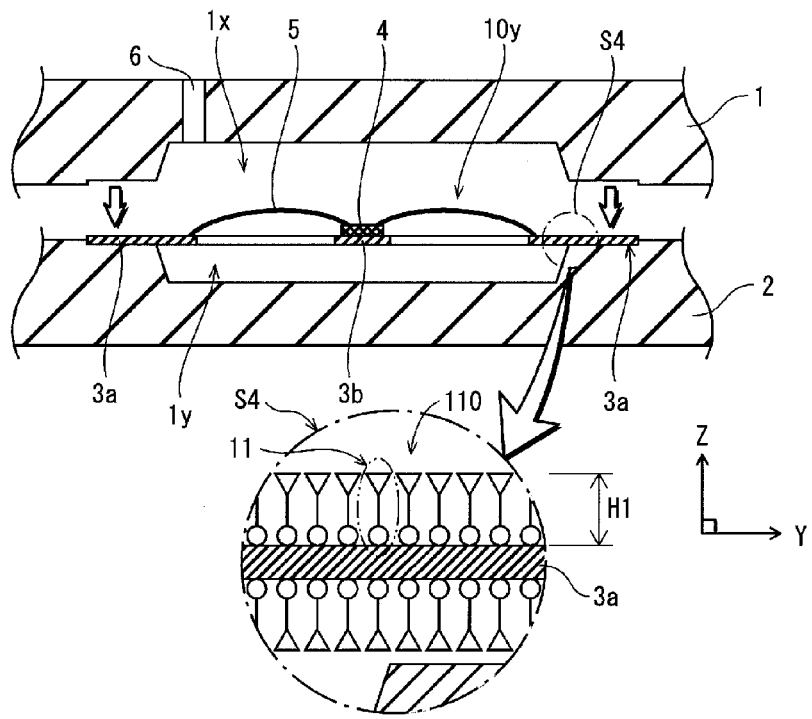
FIGS. 4A and 4B show the resin adhesion processing pertaining to Embodiment 1.

Next, a movable mold 1 is moved in the direction indicated by the arrows of FIG. 4A so as to close the molds 1 and 2. At this point, the second functional groups C1 of the functional organic molecules 11 on the surfaces of the leads 3 of the chip-bearing wiring member 10y are oriented to face the exterior and a minute organic film 110 of monomolecular thickness H1 is formed thereupon (see enlargement S4 of FIG. 4A). The region of formation of the organic film 110 includes regions not directly adjacent to the cavities 1x and 1y (inner space) within the molds 1 and 2. That is to say, the surface area of the organic film 110 extends over a greater area than that which is to be resin-sealed.

(Resin Filling Sub-Processing)

The molds 1 and 2 are heated, while closed, to a predetermined temperature. Thermosetting resin in liquid state is then injected (injection molding) with uniform pressure through a gate 6 into the cavities 1x and 1y. The resin is injected until the cavities 1x and 1y are densely filled therewith, the region including the semiconductor chip 4 of the chip-bearing wiring member 10y being at the center thereof. The resin is then hardened by the action of heat from the molds 1 and 2 (see FIG. 4B). After a certain time, if the resin has completely hardened, then resin-sealing formation is complete and a QFP 10z is thus obtained. Afterward, the outer leads 301a are bent to produce the finished QFP 10.

Figure 4B:
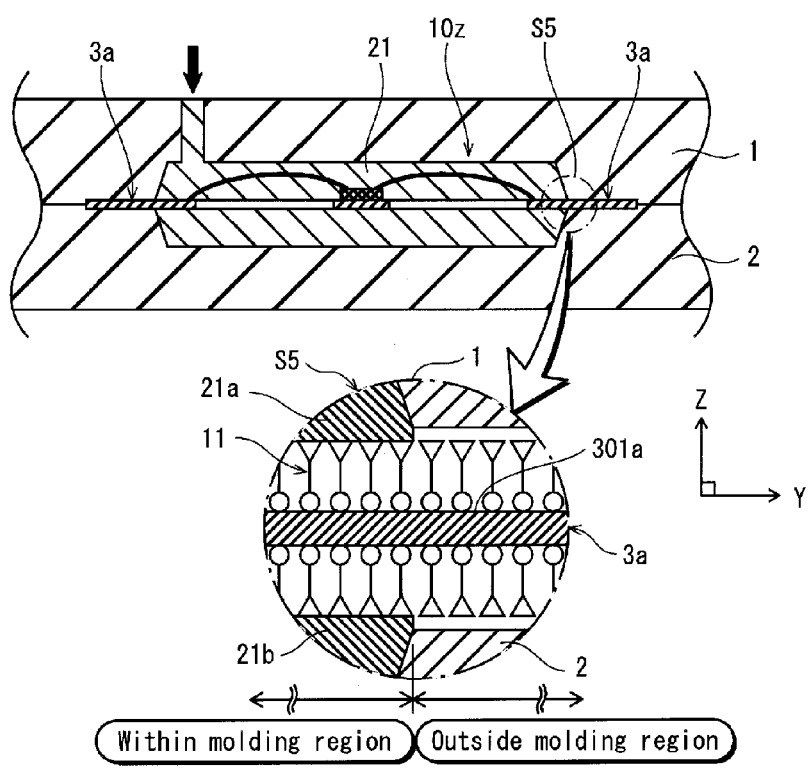

In this processing, the part of the resin injected into the cavities 1x and 1y that comes in contact with the organic film 110 is affected by the second functional group C1 (which causes or enhances hardening therein) and thus hardens comparatively faster (see FIG. 4B, within molding region).

Accordingly, the resin has nearly hardened before any part thereof can leak into any unwanted gaps adjacent to the cavities 1x and 1y that may exist at the juncture of the molds 1 and 2 (see FIG. 4B, outside molding region). Thus, resin burr formation in gaps between the molds 1 and 2 can be effectively constrained (see enlargement S5 of FIG. 4B). As a result, the formation of post resin-sealing resin burrs on the outer leads 301a of the semiconductor device can be greatly diminished. As such, conventional burr removal post-processing is rendered unnecessary, the semiconductor device can proceed more quickly to other processing, such as processing in which the device is connected to other substrates, and superbly efficient manufacturing can in turn be realized.

The QFP 10 obtained from this processing ensures stronger adhesion than offered by conventional technology between the die-pads 3a and the molded resin through the use of the organic film 110. Accordingly, when the QFP 10 is connected to other substrates, the resin will neither peel off the leads due to heat nor be damaged by cracks, despite the temperature effects of soldering and the like. Furthermore, given the hydrophoby imparted by the principal chains of the functional organic molecules and due to the minute arrangement thereof on the surface of the wiring member, results can be expected to manifest as suppression of unwanted water adsorption into the leads, suppression of surface metal ionization caused by energization, and suppression of migration.

Also, given that the organic film 110 is a monomolecular film, the thickness of semiconductor devices to which the film is applied will hardly increase at all and there is thus no risk that the volume of the resin that is to fill the cavity may not suffice due to the volume of the organic film. As such, conventional manufacturing facilities can be used while nevertheless obtaining great results from the present invention.

Figure 16A:
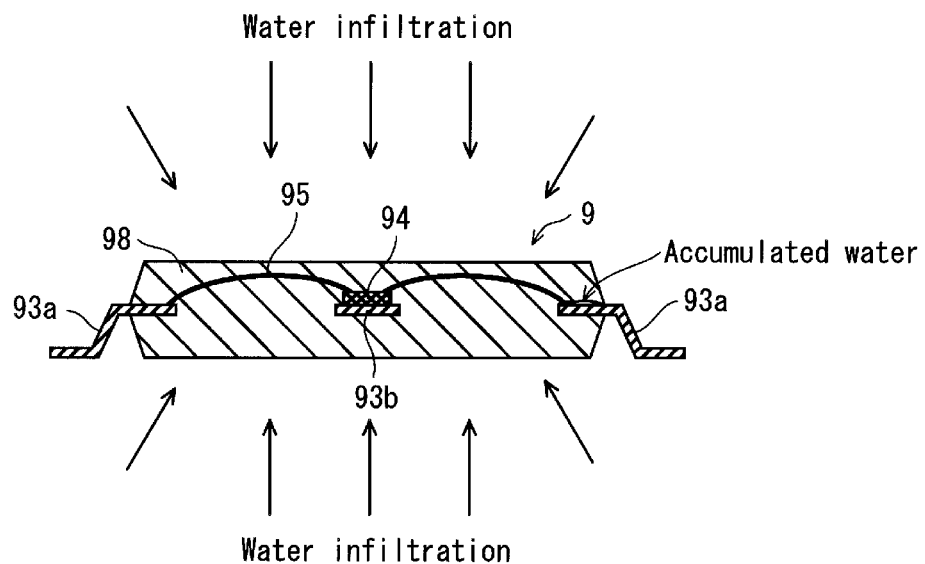
FIGS. 16A and 16B are cross-section diagrams describing the problems of a conventional semiconductor device.

As an additional result, the problems that follow from the infiltration of water into the sealing resin (molded resin), such as parts of the resin peeling away from the leads or the appearance of cracks therein, can be avoided by the QFP 10. That is to say, QFPs in general are susceptible to infiltration by ambient water into the resin due to the properties of the sealing resin (molded resin) itself (see FIG. 16A).

Figure 16B:
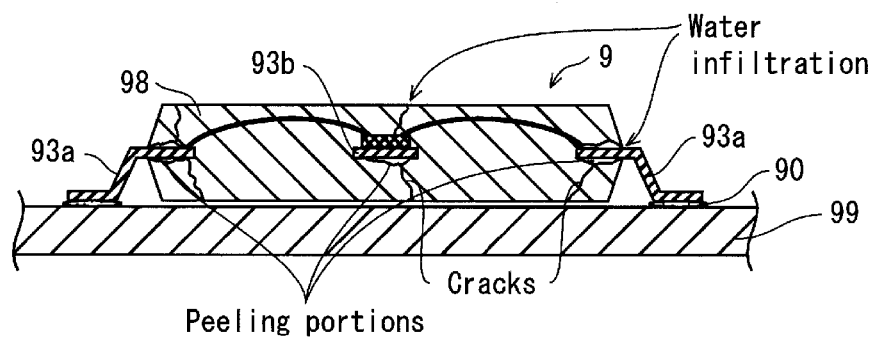

In conventional QFPs, issues may arise from the presence of gaps near the interface between the resin and the leads, such as insufficient adhesion between the two and surface metal re-crystallization in the leads when heated. The presence of such gaps facilitates accumulation by the capillary action of water seeping into the resin over time, after manufacture. When a QFP in such a state undergoes reflow heating (at approximately 260° C.) in order to be mounted on a substrate, the accumulated water is instantly vaporized, which causes a rapid expansion in volume. This sudden expansion in volume of the water within the resin cannot be resisted. Consequently, the resin in the gap portions may peel away from the leads, and cracks in the sealing resin (molded resin) may form that extend from the gaps to the surface (see FIG. 16B). Should such peeling or cracking ensue, yet more impurities, such as water, may penetrate the QFP from outside, which is a cause of circuit rupture and short-circuiting in the sealed semiconductor chip 94.

Furthermore, even if visible cracks as described above do not appear during reflow, the accumulated water in the gaps can gradually cause short-circuiting and corrosion in the semiconductor chip 94, and may render the chip inoperable.

In contrast, the QFP 10 has the organic film formed on the surface of the leads and thus the adhesion thereof to the sealing resin (molded resin) is extremely strong. This adhesiveness lasts beyond the manufacture of the QFP 10 and is superbly effective in suppressing the formation of gaps at the interface between the leads and the resin. Accordingly, even if water seeps into the sealing resin (molded resin) from the ambient air as time passes after manufacture, there are no gaps in the resin where such water can accumulate. Thus, no peeling or cracking occurs when the QFP 10 is mounted onto a substrate, such mounting can proceed with the high reliability of the sealing resin preserved, and the problem of post-mounting short-circuiting due to water is prevented from occurring.

(Metal Re-Crystallization Suppression in Lead Surfaces)

In particular, when the organic film 110 is formed of functional organic molecules with principal chains B11 (having a N-containing heterocycle containing two or more N atoms) such as the functional organic molecules 16, there is a further effect at work, explained below, in which metal re-crystallization is suppressed at the surface of the leads by anchor effects at the molecular level. This is caused by the significant stacking effects at work between the chains B11 of the functional organic molecules forming the organic film, and is superb for improving the adhesion between the leads and the sealing resin.

FIGS. 5A and 5B are diagrams explaining the effects of suppression of metal re-crystallization by a film made up of the functional organic molecules 16.

FIGS. 5A and 5B show a film made up of functional organic molecules formed upon a metal surface.

As shown in the figures, the metal surfaces of leads and the like normally feature fine undulations in addition to internal stresses. Formation of a film by arranging functional organic molecules on such a metal surface results in a film that, in turn, follows these undulations.

Then, when heat is applied to the metal of leads and the like after film formation, the undulations thereof change shape and re-crystallize as the internal stresses are relaxed. Ag plating is particularly prone to such shape-shifting.

At this time, the metal atoms move as indicated by the arrows in FIG. 5A, and given that this entails applying energy to move the functional organic molecules that have formed bonds with the metal atoms, defects (gaps) appear in the film. Once defects appear in the film, problems arise with regard to diminished adhesion between the resin and the leads as well as to changes in metallic luster.

In contrast, despite the presence of the same undulations, when the organic film 110 is formed of functional organic molecules with principal chains B11 (with a N-containing heterocycle containing two or more N atoms) such as the functional organic molecules 16, the functional organic molecules 16 cannot easily be moved because of the significant stacking effects at work between the chains B11 of the functional organic molecules forming the organic film, which persists despite the input of energy to move the functional organic molecules 16 as heat is applied to the leads.

Accordingly, defects (gaps) do not form in the film. In addition, the bonds between the functional organic molecules 16 and the metal atoms serve to suppress movement thereof, thus reducing undulation in the metal surfaces.

That is to say, the functional organic molecules 16 produce molecular-level anchor effects that suppress motion in the metal atoms and thus, can in turn suppress metal re-crystallization.

Considering that this molecular-level anchor effect from the functional organic molecules is stronger in the principal chains B11 near the first functional groups A1 (located near the root), formation of bonds is preferred in which the first functional groups A1 neighbor the principal chains B1, as is the case for the functional organic molecules 16.

Such molecular-level anchor effects in the functional organic molecules are obtained through the presence of a N-containing heterocycle containing two or more N atoms in the principal chains. Thus, a similar anchor effect can be obtained even if the functional organic molecules have no principal chains B12.

(Specific Examples of Functional Organic Molecules 11 and 16)

A specific example of one of the functional organic molecules 11 is given by the compound in the below-inscribed Chem. 1 (in which m and n are natural numbers).

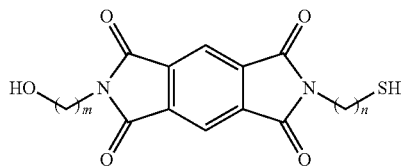

(Chem. 1)

Here, the first functional group is a thiol group, the second functional group is a hydroxyl group, and portions of the principal chain are made up of aromatic imides.

Figure 19:
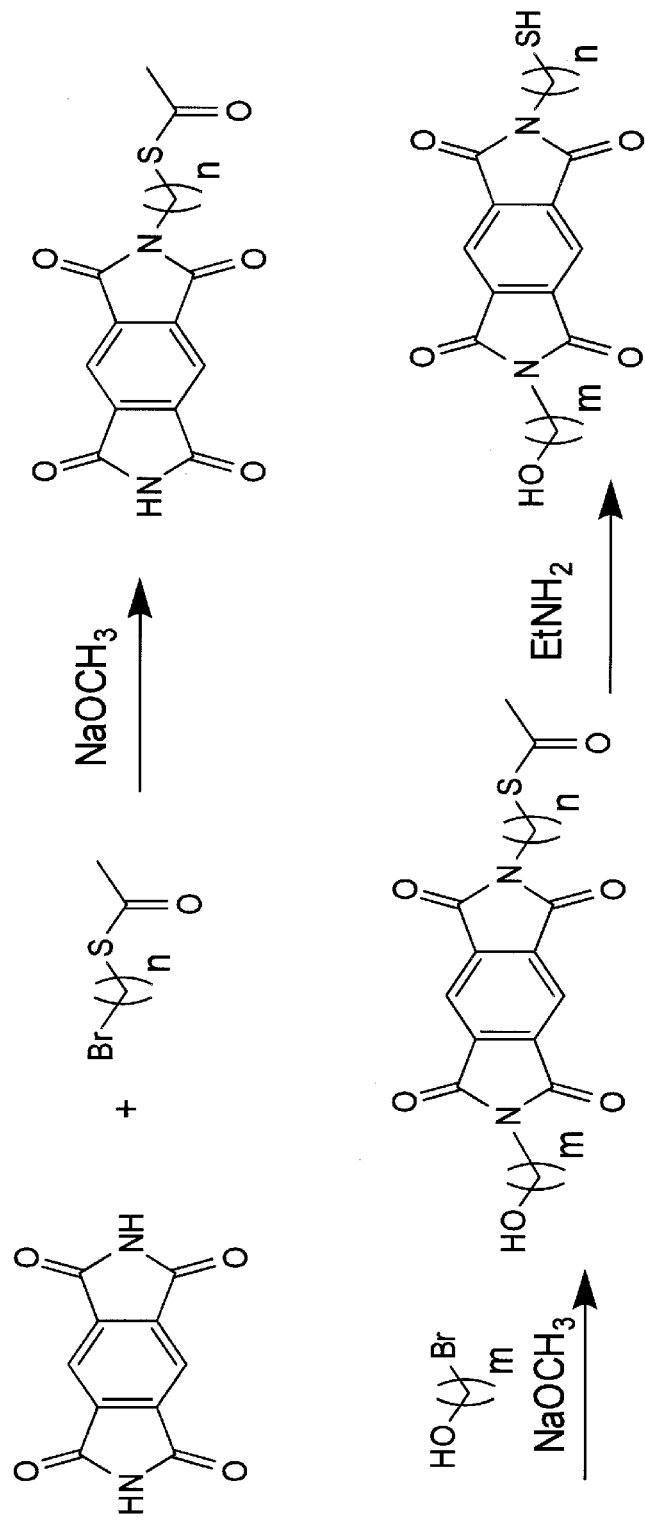
FIG. 19 shows an example of the manufacturing method of the organic molecules 11.

FIG. 19 shows one example of a manufacturing method for the functional organic molecules 11 using the above-inscribed Chem. 1.

As shown, first, pyromellitic diimide and bromomethylene acetyl sulfide are reacted in the presence of $NaOCH_3$ for an elimination reaction of an equivalent quantity of hydrogen bromide. Next, hydroxy bromomethylene is reacted in the presence of $NaOCH_3$. Afterward, the acetyl sulfide part is replaced by thiol through reaction with ethyl amine, and thus the desired compound is synthesized.

A specific example of one of the functional organic molecules 16 is given by the compound in the below-inscribed Chem. 2.

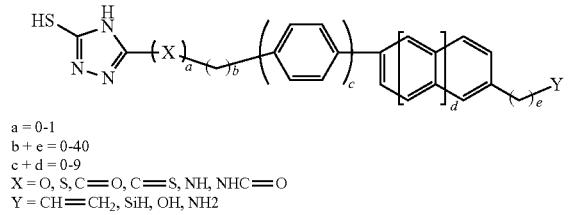

(Chem. 2)

a = 0-1
b + e = 0-40
c + d = 0-9
X = O, S, C═O, C═S, NH, NHC═O
Y = CH═$CH_2$, SiH, OH, NH2

In this example, the first functional group is a thiol group; the second functional group is a vinyl group, hydrogensilane, a hydroxyl radical, or a primary amine; the principal chain B11 is triazole; and the principal chain B12 has an aryl skeleton, an acene skeleton, or some combination of the two.

Figure 20:
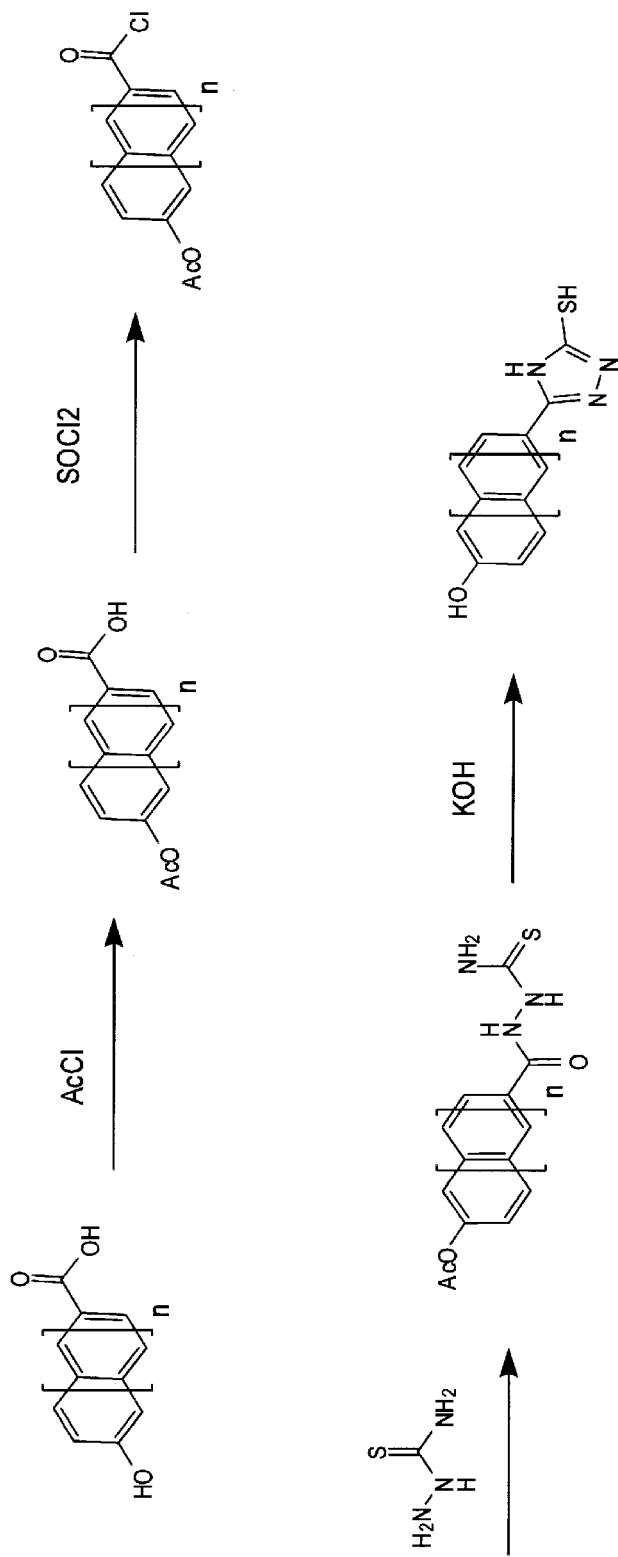
FIG. 20 shows an example of the manufacturing method of the organic molecules 16.

FIG. 20 shows one example of a manufacturing method for the functional organic molecules 16 using the above-inscribed Chem. 2. In this example, the functional organic molecules are synthesized with a structure such that the first functional group is a thiol group, the second functional group is a hydroxyl radical, the principal chain B11 is triazole, and the principal chain B12 has an acene skeleton.

As shown, first, acene carboxylic acid with terminal hydroxyl radicals has the hydroxyl radicals thereof acetylated by acetyl chloride. Then, carboxylic acid is transformed into carboxylic acid chloride using thionyl chloride. Afterward, thiosemicarbazide is used to produce bonds between the carboxylic acid chloride and amide. Once this is done, the desired compound can be synthesized by either generating triazole thiol rings using potassium hydroxide, or by generating hydroxyl radicals by de-protecting the acetyl.

Figure 21:
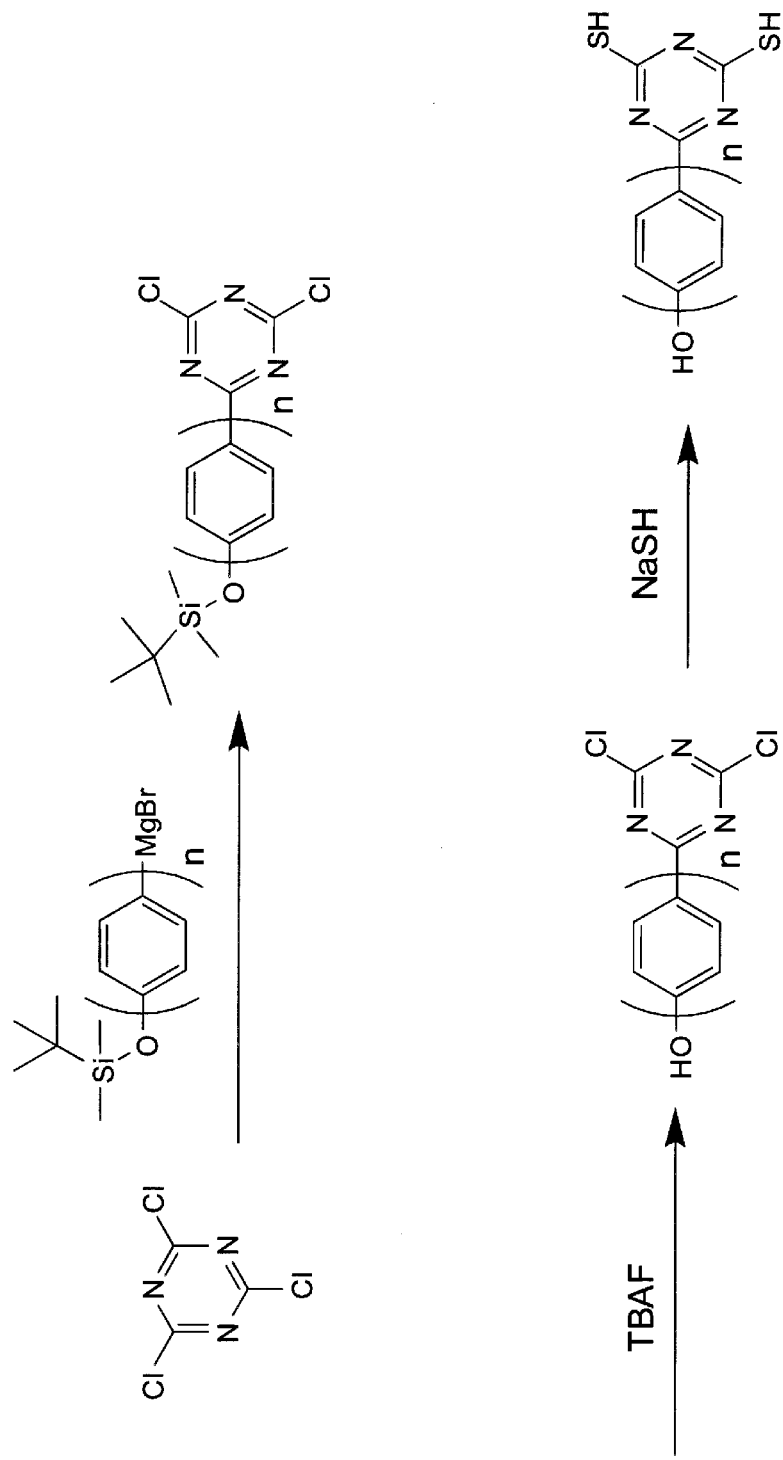
FIG. 21 shows another example of the manufacturing method of the organic molecules 16.

FIG. 21 shows another example of a manufacturing method for the above-described functional organic molecules 16. Here, the functional organic molecules are synthesized with a structure such that the first functional group is a thiol group, the second functional group is a hydroxyl radical, the principal chain B11 is triazine, and the principal chain B12 has an aryl skeleton.

As shown, and according to the content of Org. Lett., Vol. 10, No. 5, 2008, cyanuric chloride is coupled in tetrahydrofuran with brominated aryl silyl ether that has undergone a Grignard reaction. Then, hydroxyl radicals are generated by deprotecting the tert-butyl dimethyl silyl groups using fluoride tetra-n-butyl ammonium. Finally, the desired compound can be synthesized by using sodium sulfide to replace the chlorine with thiol.

[Embodiment 2]

In Embodiment 1, the organic film 110 made up of the functional organic molecules 11 is applied to a semiconductor device that comprises a semiconductor chip to produce various effects. The present Embodiment is, however, applicable to a light-emitting diode (LED) device that comprises an LED.

Figure 6:
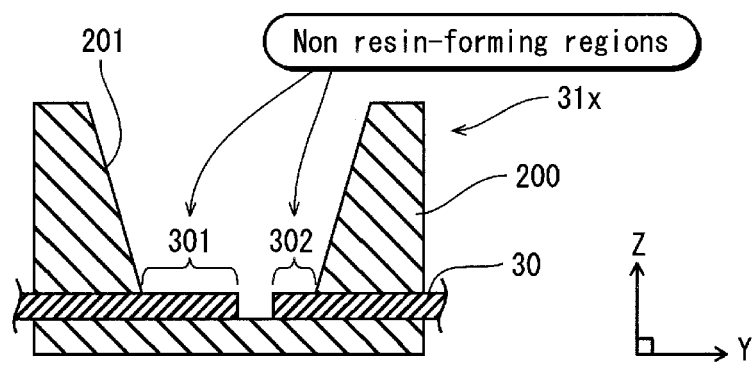
FIG. 6 shows the configuration of the LED device pertaining to Embodiment 2.

FIG. 6 is a schematic cross-section diagram showing the configuration of the lead unit 30 and the reflector 22 of the LED unit 31x pertaining to Embodiment 2.

The unit 31x is composed of a lead unit 30 arranged at the bottom of a mortar-shaped reflector 22. The reflector 22 is formed by resin molding, such as with thermosetting resin (epoxy, silicone, or similar resin). Alternatively, the reflector 22 may be formed from ceramic.

The problem of resin burr formation persists in the LED unit 31x, much like in Embodiment 1. That is, regions 301 and 302 of the lead unit 30 are exposed at the bottom of the reflector 22, and the conductivity thereof must be preserved in order to later mount the LED chip 42 thereupon (see FIG. 7A). However, due to similar principles as those explained in Embodiment 1, resin burrs may form on the exposed regions 301 and 301 at resin formation time in the gaps found between the fringe of the reflector 22 and the molds. Thus, separate burr removal processing is necessitated and the LED chip cannot be properly and effectively mounted.

Through preemptive formation of the organic film 110, itself made up of the functional organic molecules 11 or 16, at least over the surfaces of the exposed regions 301 and 302 of the lead unit 30 before the resin adhesion processing, the thermosetting resin can be made to harden faster at resin formation time. Thus, resin can be prevented from overflowing beyond the fringe of the reflector 22 and the above-described issues arising from resin burr formation can in turn be resolved.

(Supplement to Embodiments 1 and 2)

In Embodiments 1 and 2, hardening of thermosetting resin is facilitated through the use of the organic film 110. This effect can also be used for the strong formation of fine resin patterns.

For instance, precise resin formation is sometimes desired in technological fields where localized resin formation is performed on part of the surface of a wiring substrate using an inkjet method or similar. In such cases, resin formation can be performed faster through formation of organic film beforehand in comparison to direct resin formation on the lead unit 30. The merits are that less time is required for hardening, damage is less likely to occur due to liquid drops of resin or loss of shape after application, and resin molding can be formed to match precise design patterns.

Furthermore, the organic films of Embodiments 1 and 2 are not limited to direct formation on the die-pads or on the lead unit, but may also be, for instance, formed over die-pads or lead units on which plating has been previously applied. However, in such cases, the first functional group A1 should be selected so that bonds with the plating can be formed thereby.

[Embodiment 3]

The explanation of Embodiment 3 is focused on the points of difference thereof with Embodiment 2.

(LED Device Structure)

Figure 7A:
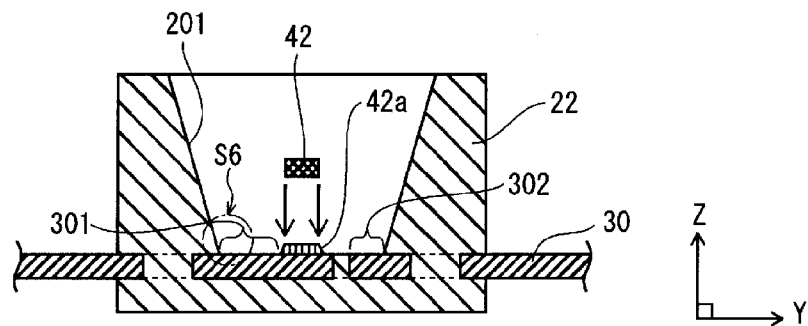
FIGS. 7A through 7C show the configuration and manufacturing processing of the LED device pertaining to Embodiment 3.
Figure 7B:
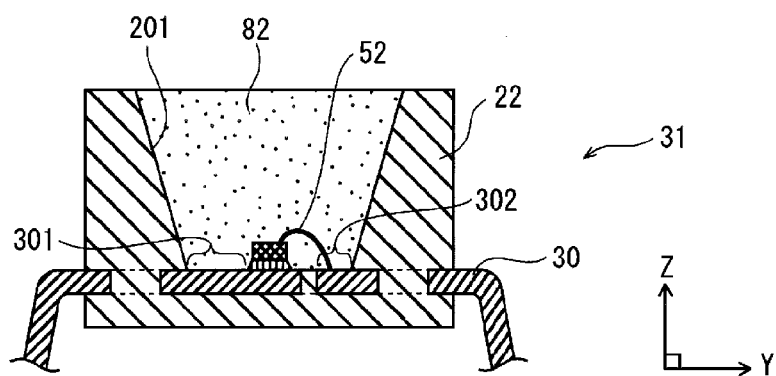
Figure 7C:
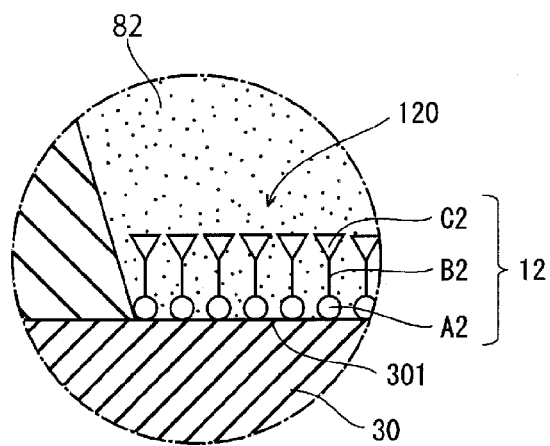

FIGS. 7A through 7C are cross-sectional diagrams showing the configuration and manufacturing process of the LED device 31 pertaining to Embodiment 3.

The LED device 31 basically comprises the LED unit 31x of Embodiment 2 where, as shown in FIG. 7A, the LED chip 42 is joined by paste 42a onto the lead unit 30 enclosed by the reflector 22. The LED chip 42 is connected to the lead unit 30 via the wire 52

The reflector surface 201 on the inside of the reflector 22 as well as the exposed regions 301 and 302 are filled in with transparent sealing resin 82 so that the LED chip 42 and other components are sealed thereby.

Silicone resin, an example of a thermosetting resin, is used as the sealing resin 82.

As such, in Embodiment 3, the surfaces of the exposed regions 301 and 302 of the lead unit 30 feature an organic film 120 formed thereon through self-assembly of functional organic molecules 12 into a monomolecular film. The general formula of the functional organic molecules 12 is expressed as A2-B2-C2. The principal chain B2 features a first functional group A2 that is able to bond with metals at one end, and features a second functional group C2 that is able to bond with silicone resin at the other end (see FIG. 7C). The principal chain B2 is similar to the principal chain B1 and the first functional group A2 is similar to the first functional group A1, both explained in Embodiment 1.

(Second Functional Group C2 of Functional Organic Molecules 12)

The second functional group C2 of each of the functional organic molecules 12 of Embodiment 3 is a functional group, chemical compound, or structure able to induce hardening in thermosetting resins, particularly in silicone resin. Specifically, this may be a vinyl group, organic hydrogen silane, or a chemical compound, structure, or derivative thereof containing one or more of the above.

Also, for silicone resin that includes one or more members selected from the group consisting of an epoxy group and an alkoxysilyl group, a functional group, chemical compound, or structure is used that can bond with the epoxy group or alkoxysilyl group. Specifically, any chemical compound, structure, or derivative thereof that includes one or more members selected from the group consisting of a hydroxyl radical, acid anhydride, primary amine, and secondary amine may be used. Given the hydrophily of such a functional group, chemical compound, or structure that can bond with the epoxy group or alkoxysilyl group, the effect is control of adhesion to the later-described hydrophobic outgas components.

A hydrophilic additive that includes an epoxy group or alkoxysilyl group may be combined with the resin components of the sealing resin 82 as an adhesion stimulant in order to enhance the bonding power of the second functional group C2. Thus, better adhesion can be obtained between the lead unit 30 and the sealing resin 82. Also, the silicone resin may be a transparent resin modified with epoxy groups or alkoxysilyl groups to obtain a hydrophilic effect. Further, the bonding networks of the second functional groups C2 with the sealing resin can be strengthened through application onto the former of a silane coupling agent that includes an alkoxysilyl group before sealing.

Given the greater stability of a functional group, chemical compound, or structure that can bond with epoxy groups or alkoxysilyl groups as described above in comparison to that of a vinyl group or of organic hydrogen silane, the stability and longevity of the functional organic molecules can in turn be enhanced.

According to the above structure, Embodiment 3 can prevent peeling of the silicone resin from the lead unit 30 through the intervention of an organic film 120 made up of functional organic molecules 12 that each include the above-described first functional group A2 and second functional group C2.

In other words, while offering superb transparency and resistance to fading in comparison to epoxy resin and the like, silicone resin is easily deformable under high temperatures due to a high rate of thermal expansion, and as such presents the risk of being peeled off or removed from the lead unit 30.

In contrast, through the formation of the organic film 120 made up of the functional organic molecules 12 as described above, the adhesion between the lead unit 30 and the silicon resin can be markedly improved.

Further, strong bonds are present between neighboring principal chains B2 of the functional organic molecules 12 that make up the organic film 120. Thus, the organic film 120 also offers minute stability when exposed to heat.

Accordingly, peeling and removal of silicone resin from the lead unit 30 can be controlled, despite considerable heat-induced deformation thereof. As such, the LED device 31 can be expected to perform reliably in high-temperature prone environments and for long periods of use.

Furthermore, in Embodiment 3, wire non-adhesion can be prevented in the bonded wire 52 that connects the LED chip 42 and the lead unit 30, and the reliability of wire bonding can be improved as a result.

That is, apart from the above-described thermosetting resin, PPA (polyphthalamide), LCP (liquid crystal polymer), or other such thermoplastic resins are occasionally used as the resin of the reflector 22. Aside from the principal thermoplastic resin components thereof, various additives such as thermal stabilizers, photo-stabilizers, fillers, lubricants, white pigments, and so on may be mixed within. When such resin is heated to liquefaction for injection molding, volatile components of any additives mixed within are outgassed into the atmosphere. Outgas from lubricants and from the base resin adheres to the surface of the lead unit and forms a thin film (film impurities) thereupon. If film impurities are present on the surface of the lead unit, then at wire bonding time, the tip of the wire may be unable to bond properly with the lead unit, and even if bonding succeeds for a time, the strength of such a bond may prove insufficient, with the result that light vibrations may induce wire non-adhesion at a later time. The presence of film impurities can be verified through use of a SEM or the like.

In contrast, the present Embodiment features the organic film preemptively formed over surface regions of the lead unit 30 and can thus prevent the formation thereupon of film impurities as a result of outgassing. Given the hydrophoby (lipophily) of the outgas from the lubricants and the base resin, if the organic film 120 made up of the organic molecules 12 is in place, then the hydrophily of the second functional group C2 comes into effect, and thus nearby hydrophobic outgas reacts to the second functional group C2 and is repelled. As such, the formation of film impurities on the lead unit 30 can be extremely effectively eliminated. Also, while the wire 52 is connected to the lead unit 30 through the organic film 120, the thickness of the organic film 120 is only that of a single organic functional molecule 12, whereas the diameter of the wire 52 is comparatively far thicker, being approximately 20 to 30 µM (approximately 2000 to 3000 times the thickness of the organic film). Accordingly, at bonding time, the few functional organic molecules 12 present in the bonding region are easily melted and dispersed through the wire by the bonding load and supersonic wave energy, and thus are merely melted into the metal joint. Thus, the wire 52 and the lead unit 30 can bond well.

Thus, according to the present Embodiment, defects due to outgassing can be avoided and more reliable joining can be obtained from wire bonding in comparison to conventional technology.

In order for good bonding to occur, the organic film should at least be formed over surface areas of the lead unit 30 where wire bonding will occur. Partial formation of the organic film can be accomplished through widely-known masking techniques on the lead unit 30 and immersion into the dispersion fluid, as shown in FIG. 3B.

Also, if Ag plating is to be formed on the surface of the lead unit 30, then the organic film can be applied over such plating. In such a case, the organic film protects the Ag plating from any reactive gasses or catalysts outside, and thus the reflective properties of the Ag plating can be maintained.

The present Embodiment may substitute the principal chain B2 of the above-described organic functional molecules 12 with the principal chain B11 explained for Embodiment 1 (with a N-containing heterocyclic compound containing two or more N atoms) or with the principal chain B12 explained for Embodiment 1 (including one or more members selected from the group consisting of an aryl skeleton, an acene skeleton, a pyrene skeleton, a phenanthrene skeleton, and a fluorene skeleton).

Figure 8:
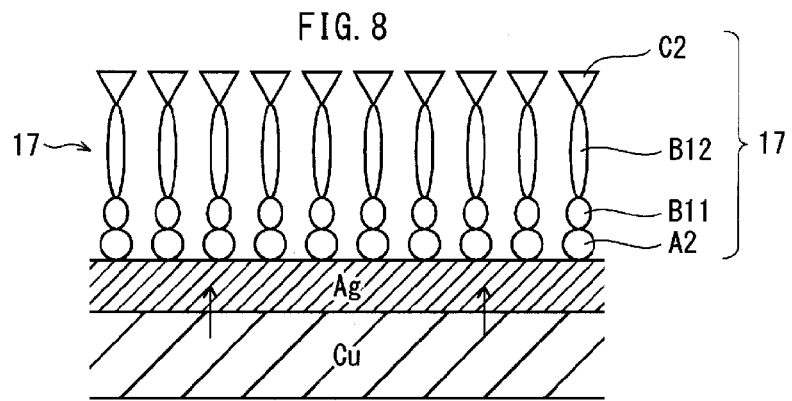
FIG. 8 describes the effects of the functional organic molecules 17.

For example, as shown in FIG. 8 with the functional organic molecules 17, the first functional group A2, principal chain B11, principal chain B12, and second functional group C2 can be used together, bonded in that order.

As explained in Embodiment 1, molecular-level anchor effects are at work when using the principal chain B11 in the functional organic molecules, and thus surface diffusion can be prevented in Ag plating applied to a Cu base metal or the like.

FIG. 8 is a diagram explaining this effect. In the lead 30, Ag plating is formed over a base layer of Cu, and the organic film made up of functional organic molecules 17 is formed over the Ag plating.

Generally, when heat is applied to the lead unit 30, the grain boundary of the Ag layer is opened wide, and as shown by the arrows in FIG. 8, the base Cu attempts to diffuse through the grain boundary of the Ag plating to the surface thereof. Then, once the Cu diffuses to the surface of the Ag layer, CuO is generated there causing discoloration in the Ag layer and worsening the wire bonding. The diffusion of Cu toward the surface of the Ag layer can be prevented through thickening of the Ag layer, but this imposes costs in terms of increased Ag volume.

In addition, surface crystallization at work in the Ag modifies the luster thereof, which has negative effects on the optical properties of the LED device.

In contrast, through formation of an organic film using the functional organic molecules 17 with principal chains B11, molecular-level anchor effects result as explained for the functional organic molecules 17 of Embodiment 1, suppressing the opening of the Ag grain boundary. Accordingly, discoloration of the Ag layer can be prevented and wire bonding can be maintained, even for a thin Ag layer. Also, through suppression of surface re-crystallization in the Ag layer, no negative effects on the optical properties of the LED device are produced as there is no change in Ag luster.

Further, even if the Cu does diffuse to the surface of the Ag layer, the principal chains B11 of the functional organic molecules 17 form a complex with the diffused Cu. This, too, is helpful for the preservation of wire bonding.

While this example is given for a case where the lead unit 30 is a Ag-plated product, the same effects can be obtained for a Au-plated or other precious metal-plated product.

Next, the effects of an organic film made up of functional organic molecules are explained for a case where the functional organic molecules 17 have a principal chain B12.

The principal chain B12 comprises one or more members selected from the group consisting of an aryl skeleton, an acene skeleton, a pyrene skeleton, a naphthalene skeleton, and a fluorene skeleton. The above allow visible light to pass through while absorbing UV light.

Accordingly, the organic film on the lead unit 30 is able to absorb the UV spectrum while allowing the visible spectrum to pass through. Thus, a UV protection effect is imparted through the absorption by the organic film of UV rays coming from outside, and in addition, visible light can be efficiently reflected by the lead unit 30.

Generally, Ag plating has a tendency toward surface degradation (i.e. blackening due to generation of AgO) in response to UV rays from outside. However, the result of the UV protection imparted by the above-described organic film is such that blackening is suppressed in the Ag plating.

Accordingly, superb long-term reliability and high luminescent efficacy can be realized in the LED device.

(LED Device Manufacturing Method)

The LED device is manufactured by realizing each of the following processes, in order. With the exception of the organic film formation processing, other known LED device manufacturing methods are also applicable.

[Organic Film Formation Processing]

An organic film 120 is formed on the surface of the lead unit 30 through self-assembly of functional organic molecules 12 into a monomolecular film in the same manner as described for the organic film formation processing of Embodiment 1. Thus, a lead unit 30 on which an organic film has formed can be obtained.

[Resin Adhesion Processing]

Using the above-described lead unit 30 on which the organic film has formed, polyphtalamide resin or similar thermoplastic resin is injection molded thereon using an injection process similar to that shown in FIGS. 4A and 4B. Afterward, the surrounding area is cooled to a fixed temperature in order to harden the resin. Thus, the reflector 22 is formed and the LED unit 31x is obtained.

Next, the LED chip 42 is mounted onto the lead unit 30 with paste 42a. Then, the lead unit 30 and the LED chip 42 are bonded to each other via the wire 52.

Afterward, the reflector 22 is filled in with silicone resin in liquid state. The LED device 31 is obtained from thermal hardening thereof.

[Embodiment 4]

Figure 9A:
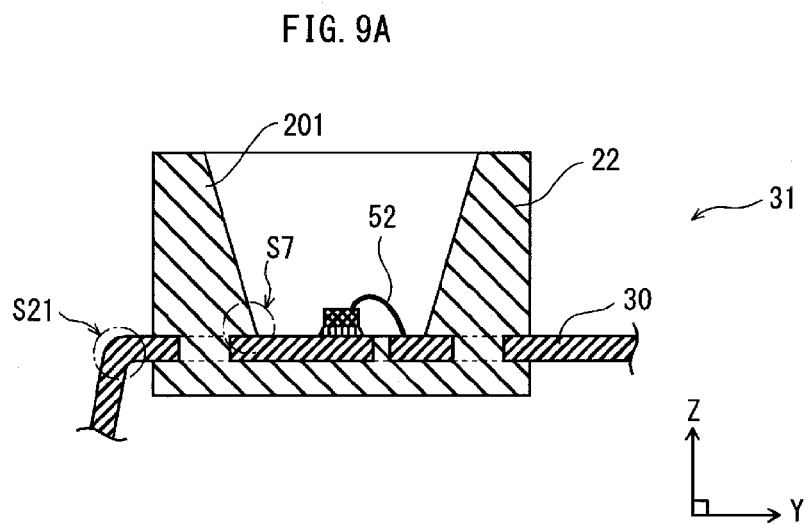
FIGS. 9A and 9B show the configuration of the LED device pertaining to Embodiment 4.

FIG. 9A is a cross-section diagram showing the configuration of the LED device 31 pertaining to Embodiment 4.

The explanation of the LED device 31 of the present Embodiment is focused on the points of difference thereof with Embodiment 3.

In Embodiment 3, a functional group able to chemically bond with silicone resin was specially selected as the second functional group C2 of the functional organic molecules 12 that make up the organic film 12. However, in Embodiment 4, a functional group characterized by instantaneous hardening is specially selected as the second functional group C2' of the functional organic molecules 12a that make up the organic film 120a.

Specifically, any chemical compound, structure, or derivative thereof including one or more members of the group consisting of a Pt complex, a Pd complex, a Ru complex, and a Rh complex may be used as the second functional group C2'.

The manufacturing method of the LED device 31 pertaining to the present Embodiment is similar to that given for the above-described Embodiment 3.

The effects of the LED device 31 are explained below.

The reflector 22 is prepared through injection molding of thermoplastic resin such as polyphthalamide resin. However, when the thermoplastic resin is cooled and hardened, volumetric shrinkage thereof may occur. Should this occur, gaps 72 may appear between the lead unit 30 and the reflector 22 (see FIG. 9B).

If such gaps 72 appear, excess overflow resin 82a is likely to result at silicone resin filling time, which is a waste of material. Also, given that overflow resin 82a is linked to electrical bonding deterioration in the outer leads of the lead unit 30, separate removal processing is later necessitated, which leads to a decline in manufacturing efficacy. Furthermore, if the overflow resin 82a comes between the LED device 31 and the heat sink (not diagrammed) affixed to the back thereof, the head dispersal capabilities of the heat sink may be negatively impacted.

In contrast, in Embodiment 4, the second functional group C2' of each of the functional organic molecules 12a has instantaneous hardening properties. Thus, during the manufacturing process, the silicone resin that fills the inside of the reflector 22 hardens soon after filling.

Furthermore, due to the strong bonds between principal chains B2 of each of the functional organic molecules 12a that make up the organic film 120a, the organic film 120a is minute and stable under heat.

The result is such that solid silicone resin is formed sooner at the bottom of the mortar-shaped reflector 22, sealing off the gaps 72. Thus, the silicone resin that subsequently fills the reflector 22 can be effectively prevented from overflowing through the gaps 72. Accordingly, there is no need for conventional separate processing for overflow resin 82a removal, and manufacturing efficacy can be enhanced as much.

Furthermore, as there is no chance that overflow resin 82a will adhere to the outer leads of the lead unit 30, no damage is done to the capability thereof to electrically connect to the outside. Thus, after high-reliability soldering or the like, an electrically connective LED device 31 can be obtained.

Also, by preventing the overflow of silicone resin through the gaps 72, the air in the gaps 72 can be controlled so that the air does not mix with the silicone resin and create a void (air bubble) therein. This can serve to further enhance the sealing reliability of the silicone resin in the LED device 31.

Figure 9B:
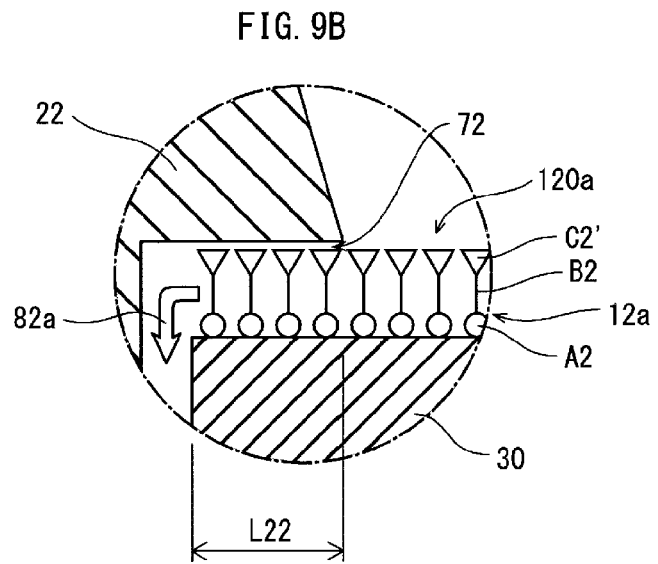

In order to obtain the above-described results, the organic film 120a should be disposed so as to reach region L22 which, as shown in enlargement S7 of FIG. 9B, extends into the gap 72 between the reflector 22a and the lead unit 30. As such, even if a quantity of silicone resin 82 flows into the gaps 72, the resin is able to harden before this quantity grows to overflow, which is ideal in preventing further overflow.

(Principal Chain of Functional Organic Molecules 12a)

As shown in FIG. 9B, each of the functional organic molecules 12a is made up of a first functional group A2, a principal chain B2, and a second functional group C2', bonded in that order. However, the functional organic molecules may also be made up of a first functional group A2, a principal chain B11, a principal chain B12, and a second functional group C2', bonded in that order, or else of a either a principal chain B11 or a principal chain B12 bonded to a first functional group A2 and a second functional group C2'.

If the functional organic molecules have a principal chain B11, then the molecular-level anchor effects described for Embodiment 1 can be obtained. Also, if the functional organic molecules have a principal chain B12, then the UV protection effects described for Embodiment 3 can be obtained.

[Embodiment 5]

Figure 10A:
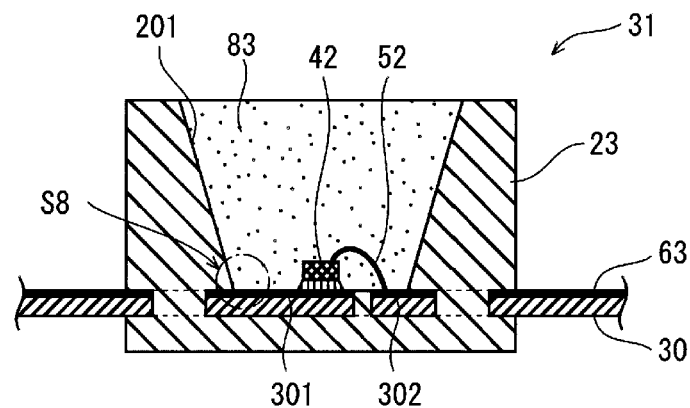
FIGS. 10A and 10B show the configuration of the LED device pertaining to Embodiment 5.

FIG. 10A is a cross-section diagram showing the configuration of the LED device 31 pertaining to Embodiment 5.

The explanation of the present Embodiment is focused on the points of difference thereof with Embodiment 4.

Figure 10B:
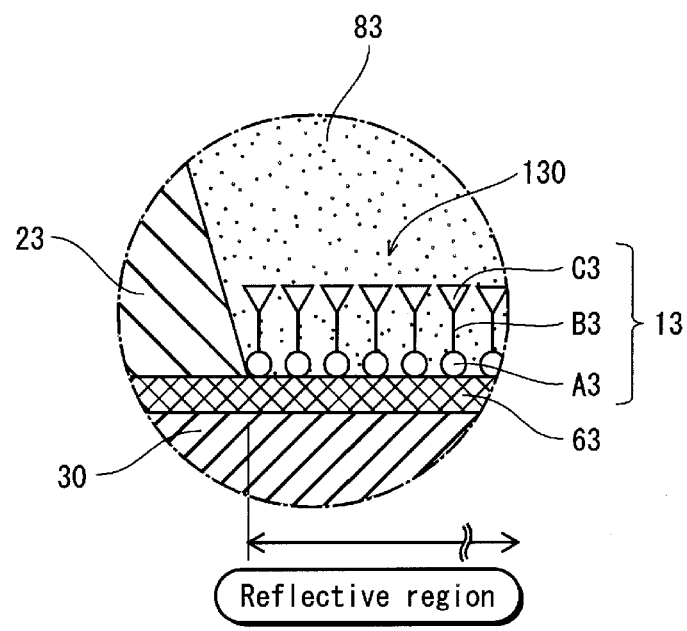

As shown in FIG. 10B, the LED device 31 of the present Embodiment has an organic film 130 made up of the functional organic molecules 13 formed thereupon.

The first functional group A3 and the principal chain B3 of each of the functional organic molecules 13 are identical to the first functional group A1 and the principal chain B1 explained for Embodiment 1. However, a fluorescent or phosphorescent functional group is specially used as the second functional group C3.

Accordingly, the luminescent efficacy of the LED device 31 can be improved by disposing an organic film 130 with a fluorescent or phosphorescent functional group on the surface thereof.

In particular, as shown in FIG. 10A, if Ag plating 63 is formed over the surface of the lead unit 30, then as explained below, the reflectivity thereof with respect to the light emitted by the LED chip 42 can in turn be improved.

Generally, the effective reflection wavelengths for Ag are approximately 500 nm and up. Light at shorter wavelengths (on the order of 380 to 500 nm, i.e. blue light, UV light, and the like) is not effectively reflected thereby.

In contrast, in the present Embodiment, an organic film 130 is formed over the Ag plating 63 corresponding to the exposed regions 301 and 302 of the lead unit 30. The organic film 130 is made up of functional organic molecules 13 that have second functional groups C3 able to receive short-wavelength light through a fluorescent or phosphorescent functional group or structure (see enlargement S8 of FIG. 10B). Accordingly, the efficacy of the Ag plating 63 in reflecting visible light can be complemented.

In effect, when the LED device 31 is actuated, the long wavelength ($\geq 500$ nm) light portion of the light emitted by the LED chip 42 is directly reflected by the surface of the Ag plating 63 to the front face of the chip. When this occurs, due to the monomolecular-level thickness of the organic film 130, the long-wavelength light is not prevented from progressing and passes through the organic film 130, reaching the Ag plating 63 to be reflected thereby.

As for the short-wavelength light (380-500 nm wavelength light) emitted by the LED chip 42, such light does not pass through the organic film 130 due to the higher energy level thereof relative to the long-wavelength light. In the exterior-adjacent second functional group C3, the light energy (E=hv) causes the energy level of the second functional group C3 to jump to an excited state (E0→E1). As a result, the light energy (E=hv) ultimately produces visible light by inciting the fluorescence or phosphorescence of the second functional group C3.

That is to say, the short-wavelength light from the LED chip 42, while not in fact reflected by the organic film 130, is used to generate nearly identical light as fluorescence or phosphorescence via the light energy (E=hv) thereof. The result is such that the short-wavelength light as well as the long-wavelength light emitted by the LED chip is effectively utilized by the LED device, thus allowing the realization of an LED device 31 with superior lighting efficacy in comparison to conventional configurations.

It should be noted that a structure according to which another type of plating is used instead of the Ag plating 63 is also applicable to Embodiment 5. The plating directly reflects visible light and emits light through the second functional group C3, regulating the optical properties of the LED chip 42. For example, the effective reflection wavelengths for Au plating are approximately 600 nm and up. Accordingly, visible light at wavelengths in the neighborhood of 600 nm is reflected by Au plating, and additionally, the second functional group C3 emits red fluorescence or phosphorescence at wavelengths ranging from 600 to 700 nm. As such, an LED device 31 can be realized that specially enhances the brightness of red light.

(Second Functional Group C3)

The second functional group C3 is, as described above, required to have fluorescent or phosphorescent properties based on short-wavelength excitation.

For instance, any chemical compound, structure, or derivative thereof that includes one or more members selected from the group consisting of a styryl-ben derivative such as a bis-styryl-biphenyl derivative, a styryl-ben derivative with an azole such as a bis-(triazole amino)-styryl-ben-sulfone derivative, a coumarin derivative, an oxazole derivative, a pyralizole derivative, a pyrene derivative, and a porphyrin derivative may be used.

(Principal Chain of Functional Organic Molecules)

In the present Embodiment, each of the functional organic molecules 13 may be made up of a first functional group A2, a principal chain B11, a principal chain B12, and a second functional group C3, bonded in that order, or else of a either a principal chain B11 or a principal chain B12 bonded to a first functional group A2 and a second functional group C2, instead of the configuration shown in FIG. 10B.

If the functional organic molecules have a principal chain B11, then the molecular-level anchor effects described for Embodiment 1 can be obtained. Also, if the functional organic molecules have a principal chain B12, then the UV protection effects described for Embodiment 3 can be obtained.

[Embodiment 6]

Figure 11A:
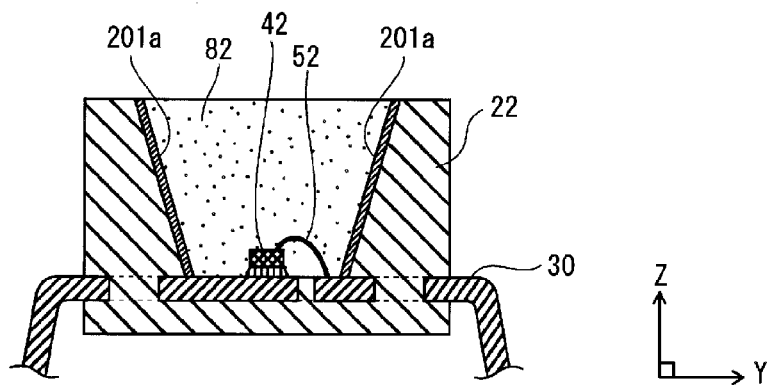
FIGS. 11A through 11C show the configuration of the LED device pertaining to Embodiment 6.
Figure 11B:
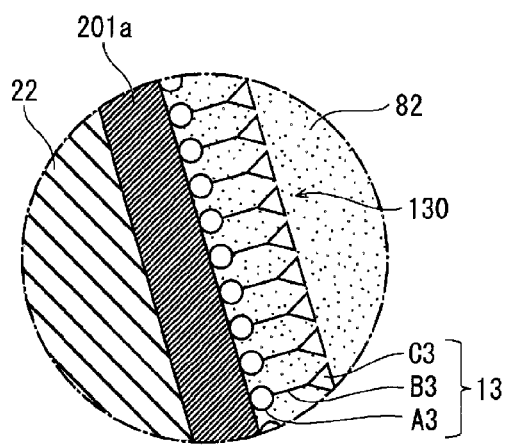

FIG. 11A is a cross-section diagram showing the configuration of the LED device pertaining to Embodiment 6.

The LED device pertaining to Embodiment 6 takes the LED device of Embodiment 4 as a base, with Ag plating 201a disposed on the surface of the reflector 22. In addition, the organic film 130 made up of the functional organic molecules 13 described for Embodiment 5 is formed over the surface thereof.

Through the presence of the Ag plating 201a on the surface of the reflector, light emitted from the sides of the LED chip 42 at actuation time is highly efficiently reflected by the plating 201a and dispersed to the front of the device (top of the figure), thereby bringing about superb lighting efficacy.

Furthermore, given that the organic film 130 is formed over the surface of the Ag plating 201a, manufacturing-time degradation of the Ag plating 201a due to unwanted gasses and UV rays can be prevented, thus preserving the reflective properties thereof.

To be precise, Ag generally has abundant chemical reactivity and thus may react with all manner of corrosive gasses present in the atmosphere during manufacturing (i.e. the various components included in the thermoplastic resin of the reflector 22) and with the catalysts for addition polymerization in the sealing resin 82, which consists of silicone resin (i.e. Pt catalysts). In addition, given that silicone sealing resin remains extremely permeable to gasses after the LED device is complete, the Ag is likely to react with corrosive gasses in the atmosphere (i.e. hydrogen sulfide). If such corrosive gasses or catalysts react with the Ag, discoloration or clouding thereof may result, in turn negatively impacting the reflective properties. Furthermore, surface degradation (blackening arising from oxidation) occurs in the Ag due to irradiation by UV rays in LED light and sunlight, which makes for diminished reflective properties relative to those present at the outset. Therefore, regardless of the light emission properties of the LED chip 42, the Ag plating is rendered unable to usefully reflect the light emitted thereby. This is problematic in that the luminescence of the device as a whole is lost and the lighting efficacy thereof is diminished.

The problem posed by light efficacy diminution due to the plating reacting with corrosive gasses and catalysts is present even if the plating is other than Ag plating.

In contrast, the LED device of the present Embodiment provides the organic film 130 over the surface of the Ag plating 201a through minute arrangement of the functional organic molecules 13.

Thus, even if corrosive gasses and catalysts are present in the atmosphere at manufacturing time, the organic film 130 works to protect the Ag plating 201a and thus, direct contact between such corrosive gasses and the Ag plating 201a is avoided. Accordingly, no unwanted reactions occur in the Ag, the superb reflective properties of the Ag plating 201a are preserved, and an LED device with great luminescent efficacy can be realized.

Also, given the excellent reflective properties of the Ag plating, the light output of the LED chip 42 can be effectively improved as any wasted output is captured in the form of latent heat by the surrounding Ag plating. Thus, according to Embodiment 6, the device can be advantageously miniaturized while retaining superb luminescent efficacy and preventing overheating damage to the LED chip 42 for a longer useful life.

Furthermore, as explained in Embodiment 5, the functional organic molecules 13 can be used for the fluorescence or phosphorescence of the second functional group C3 thereof. As such, superb luminescent efficacy can be expected to result from advantageously utilizing the high energy of short-wavelength light output by the LED chip 42 in this manner.

Figure 11C:
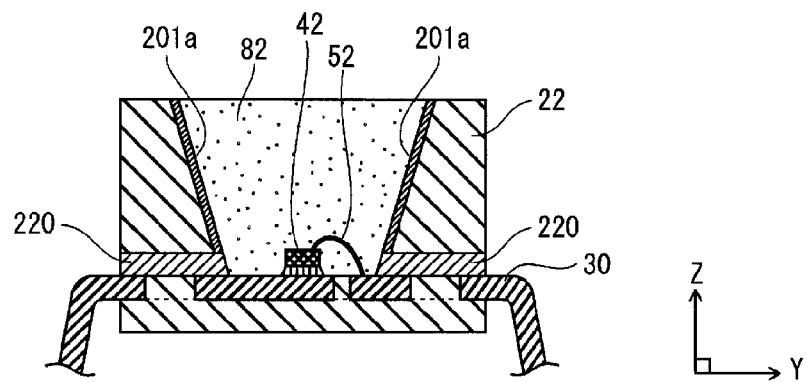

The method of formation of the organic film for the LED device of the present Embodiment may be a masking method applied to areas other than the surface of the Ag plating 201a. Alternatively, as shown in FIG. 11C, the reflector 22 may be configured as metal independent from the lead unit 30, and the Ag plating 201a may be formed on predetermined areas thereof through electroplating processing or the like. As shown in FIG. 3, the organic film 130 is formed over the entire surface through immersion in a predetermined dispersion fluid. Afterward, an insulating adhesive resin 220 (other resins or ceramic may also be used) may be interposed and affixed to the lead unit 30 to prevent short-circuiting between the reflector 22 and the lead unit 30. In such a case, the organic film 130 is formed over a wider area than that covered by the Ag plating 201a, but this poses no problems for the LED device.

(Principal Chain and Second Functional Group C3 of Functional Organic Molecules)

With respect to the principal chain of the functional organic molecules, functional organic molecules made up of a first functional group A3, a principal chain B11, a principal chain B12, and a second functional group C3, bonded in that order, or else of a either a principal chain B11 or a principal chain B12 bonded to a first functional group A3 and a second functional group C3 may be used instead of the functional organic molecules 13.

If the functional organic molecules have a principal chain B11, then the molecular-level anchor effects described for Embodiment 1 can be obtained. Also, if the functional organic molecules have a principal chain B12, then the UV protection effects described for Embodiment 3 can be obtained. Accordingly, surface degradation (blackening caused by oxidation) due to UV rays striking the Ag plating can be suppressed through this UV protection effect, and the above-described effect concerning visible light reflection can be simultaneously obtained.

As for the second functional group, instead of the functional organic molecules 13, the functional organic molecules 12 or 17, which have second functional groups C2, explained for Embodiment 3 may be used in order to prioritize improvements to the adhesion of the sealing resin 82 (silicone resin or similar) that fills the reflector 22. Also, the functional organic molecules 12 and 13 may be used together.

(Supplement to Embodiments 1 through 6)

The organic films explained for the Embodiments 1 through 6 above also provide the following effects when formed on the surface of die-pads or of a lead unit.

In a semiconductor device such as an IC or LSI, the surfaces of the leads are subjected to a roughening process to improve adhesiveness with the resin (epoxy resin) by improving the grip of the resin thereon.

Quality control of a semiconductor device so manufactured is carried out through visual inspection. This inspection is generally performed via laser measurement in which a laser device and photo-detector are used. However, roughened elements lead to unwanted irregularities in laser reflection. This, in turn, can diminish the reflective efficacy of the photo-detector or cause unwanted light to be detected, which is problematic for the precise measurements involved. Such problems are in evidence when a weak laser is used to perform minute inspections.

In contrast, if the organic film explained in Embodiments 1 through 6 is applied to the surfaces of roughened die-pads or lead units, then the functional organic molecules can absorb the laser light and use the energy thereof for conversion to fluorescent or phosphorescent light. This can, in turn, prevent irregularities in laser reflection caused by dents in the roughened surfaces. Thus, visual inspection can be carried out more accurately and efficiently, which also improves the efficiency of the manufacturing process as a whole.

Also, the LED device may use silicone resin-containing conductive paste (such as Ag paste or similar die-bonding material) instead of using silicone resin for the entirety of the sealing resin. If silicone resin-containing conductive paste is used for die-bonding of the LED chip 42, then the LED chip 42 and the lead unit 30 can be firmly joined. Also, given that silicone resin-containing conductive paste is less prone to deterioration than conventional epoxy resin-containing conductive paste, more stable electric and thermal conductivity can be expected to result.

Furthermore, the Ag particles within the Ag paste may have the organic film formed on the surfaces thereof. As such, Pt catalysts in the silicone resin for addition polymerization, unwanted corrosive gasses and the like can be prevented from coming into direct contact with the Ag particles and thus, degradation and discoloration thereof can be constrained. Accordingly, the transparency of the sealing resin 82 can be maintained and a better LED device results in which loss of luster is controlled over the long useful life thereof.

[Embodiment 7]

Embodiment 7 of the present invention is explained below.

Embodiment 7 pertains to a film carrier tape used for mounting of electronic components onto ICs, LSIs and the like, i.e. to TAB (Tape Automated Bonding) tape, T-BGA (Tape Ball Grid Array) tape, ASIC (Application Specific Integrated Circuit) tape, and the like. In particular, the present Embodiment concerns improved technology for the adhesion of a solder resist layer in such tape.

FIGS. 12A through 12F are cross-section schematic diagrams showing the manufacturing processing of the film carrier tape 40 pertaining to Embodiment 7.

Figure 12A:
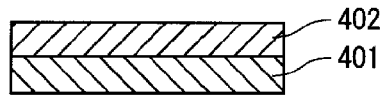
FIGS. 12A through 12F show the manufacturing processing of the film carrier tape pertaining to Embodiment 7.
Figure 12B:
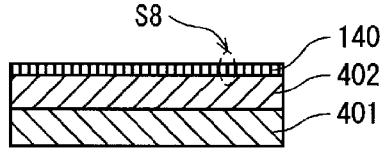
Figure 12C:
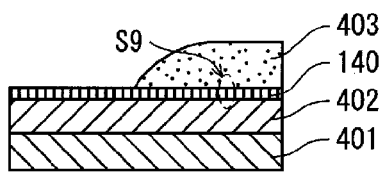
Figure 12D:
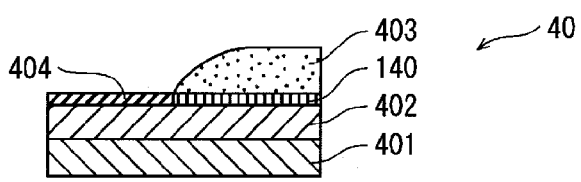

As shown in FIG. 12D, the film carrier tape 40 is composed of an insulating film 401 made up of polyimides or similar, a wiring pattern layer 402 made of Cu, and a solder resist layer 403, layered in that order.

The insulating layer 401 and the solder resist layer 403 are made of insulating resin (such as polyimide, epoxy, or urethane resin). Both are used as insulating means to prevent short circuits in the wiring pattern layer 402.

The surface of the wiring pattern layer 402 is connected by solder to the mounted components, and as such Sn plating 404 is preemptively applied thereto. Sn has certain solder wetness, pliability, and lubricity properties that make it ideal for the formation of the Sn plating 404 used in the film carrier tape 40.

When the Sn plating 404 is formed on the film carrier tape 40, the previously-prepared insulating film 401, wiring pattern layer 402, and solder resist layer 403 are layered, in that order. All of these are heated to a fixed temperature and immersed in a Sn plating vat full of Sn plating fluid (such as Sn-including compounds melted with a $BF_4$ solvent) where Sn plating is then carried out through electroplating or the like. Sn plating 404 is selectively formed over the wiring pattern layer 402 by utilizing the properties of the insulator, which are such that the material does not adhere to Sn components.

In Embodiment 7, the above-described Sn plating process is performed first, and an organic film 140 is then formed over the wiring pattern layer 402 through self-assembly of functional organic molecules 14.

Figure 12E:
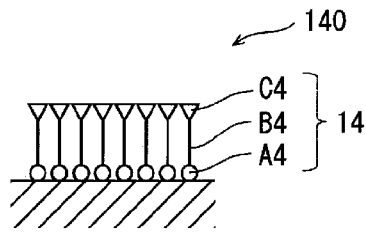

As shown in FIG. 12E, the functional organic molecules 14 are each formed of a principal chain B4 with a first functional group A4 bonded thereto at one end, and a second functional group C4 bonded thereto at the opposite end. Also, the second functional group C4 is a functional group selected for high adhesiveness to the solder resist layer 403 (for example, any chemical compound, structure, or derivative thereof including one or more members selected from the group consisting of acid phthalic anhydride, pyromellitic acid dianhydride or other such acid anhydrides, and a primary amine compound).

The first functional group A4 is identical to the first functional group A1 and the principal chain B4 is identical to the principal chain B1 respectively explained for Embodiment 1.

Figure 12F:
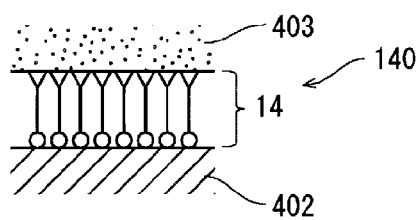

As shown in FIG. 12F, through arrangement of such functional organic molecules 14 into the organic film 140, the wire pattern layer 402 and the solder resist layer 403 are firmly bonded to each other. The ends of solder resist layer 403 will not peel away from the wiring pattern layer 402 during the Sn plating processing despite immersion in the Sn plating vat heated to a predetermined temperature. Thus, the solder resist layer 403 is prevented from peeling away, and as a result, a better Sn plating layer 404 can be formed.

Furthermore, the so-called inner battery effect can be constrained in the wiring pattern layer 402 of Embodiment 7, and thus erosion therein can be effectively prevented. The underlying principles are explained using the schematic enlargement of FIG. 17A which shows the wiring pattern layer 402 and the solder resist layer 403 during plating.

Due to the inherent linear expansion coefficients arising from the respective properties of the solder resist layer 403 and the wiring pattern 402, the solder resist contracts while hardening and internal stresses occur therein.

Given that the plating fluid in the plating vat is heated up to a point in the neighborhood of 60° C., when the wiring pattern layer 402 with the solder resist layer 403 layered thereupon is immersed in the plating fluid, thermal expansion occurs to a comparatively high degree in the solder resist layer 403, which has greater internal stresses than metal. Thus, the end portions 403x of the solder resist layer 403, being most prone to the influence of thermal contraction, curl up away from the surface of the wire pattern 402 under the influence of internal stresses. The plating fluid then infiltrates the space between the end portions 403x and the wiring pattern layer 402 and, due to remaining internal stresses in the solder resist layer 403, the end portions 403x are lifted yet higher. Principally by adding a plating fluid solvent in the space between the upraised end portions 403x and the wiring pattern layer 402, a solvent region 500 results where Sn ions are dilute.

Figure 17A:
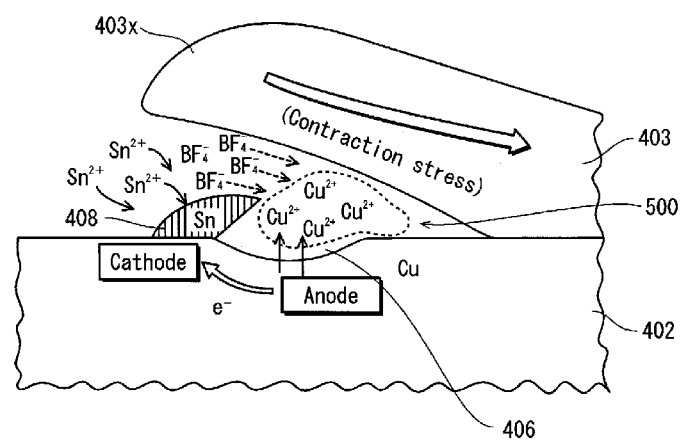
FIGS. 17A and 17B are schematic diagrams showing the configuration of conventional film carrier tape and the formation process of a local electric cell.

A concentration gradient of Sn components in the plating fluid thus arises in this solvent region 500 and in the neighboring region 501. Also, due to the different ionization tendencies of Sn and Cu, and in contrast to the solvent region 500 in which Sn ions are dilute, Cu ions are dissolved out of the surface of the wiring pattern layer 402. As Cu ions are created, the electrons released from the wiring pattern layer 402 are taken up by the Sn ions in the plating fluid, and an accumulative layer 408 of deposited Sn is thus formed in the region of the wiring pattern layer 402 directly below the end portions 403x of the solder resist layer 403. Through a chain of redux reactions by the Sn and Cu ions, a so-called local electric cell is formed as shown in FIG. 17A (see Japanese Patent Publication No. 3076342 for more on the formation process of the local electric cell).

Figure 17B:
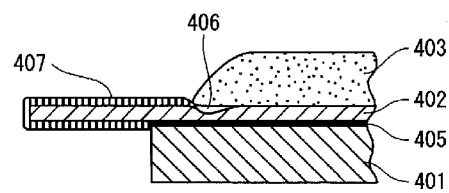
Figure 18A:
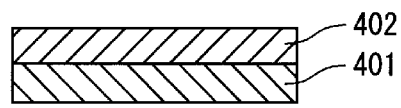
FIGS. 18A through 18D show the configuration of film carrier tape to which a double layer of Sn plating has been applied with conventional technology.
Figure 18B:
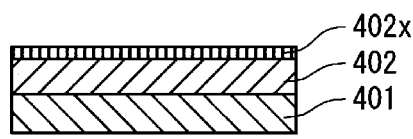
Figure 18C:
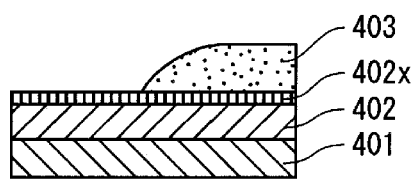
Figure 18D:
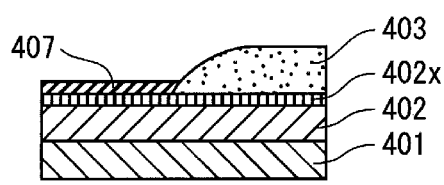

If this local electric cell reaction proceeds further, the dissolution of Cu ions leads to the formation an erosion region 406. The erosion region 406 remains, even if later covered and hidden by the end portions 403x (see FIG. 17B). Although the erosion region 406 is not noticeable from outside, the presence thereof leads to breakage and other negative consequences for the film carrier tape applied thereto due to the manufacturing-time stresses imposed by the erosion region 406 when the film carrier tape is used.

In contrast, in the present Embodiment, the organic film 140 provides strong adhesion between the solder resist layer 403 and the wiring pattern layer 402. Also, the principal chains B4 of neighboring functional organic molecules 14 that make up the organic film 140 are strongly bound to each other, and as such, the end portions 403x will not curl up away from the wiring pattern layer 402 despite the presence of certain plating-time internal stresses in the solder resist layer 403 relative to the wiring pattern layer 402. Accordingly, the formation of the erosion region 406 is avoided as the solder resist layer 403 never peels away from the wiring pattern layer 402. In addition, while thermal expansion does occur when the solder resist layer 403 is immersed in the plating vat, the internal stresses arising therefrom can be cancelled by the usual annealing processing and the like performed after plating, and so the problem of stress damage to the solder resist layer 403 is negated. Thus, according to Embodiment 7, better Sn plating 404 can be formed and a film carrier tape with superb mechanical adhesiveness can be realized.

Japanese Patent Publication No. 3076342 discloses technology for preventing the formation of the erosion region 406 by, as shown in FIGS. 18A through 18D, preemptively providing a first Sn plating layer 402x, which contains Cu components, over the surface of the wiring pattern layer 402 before arranging the solder resist layer 403 thereupon, and later providing a second Sn plating layer 407 with the formation of the solder resist layer 403. However, according to Embodiment 7, there is no need for two separate plating processes. As such, the time required for the manufacturing process can be reduced, the amount of plating material used and lost can be diminished, and manufacturing costs as well as time stand to be reduced to a noticeable degree.

(Manufacturing Process)

The manufacturing process of the film carrier tape 40 is explained below.

First, a predetermined wiring pattern layer 402 (Cu foil) is formed over the insulating film 401 using photo-etching or similar methods (FIG. 12A).

Next, the functional organic molecules 14 are made to adhere to the wiring pattern layer 402 and the organic film 140 is formed through self-assembly thereof into a monomolecular film. This constitutes the organic film formation processing (FIG. 12B).

Next, solder resist paste is applied to the organic film 140 using printing methods or the like to form the solder resist layer 403. This constitutes the solder resist layer formation processing (FIG. 12C). At this point, the second functional groups C4 cause hardening in the solder resist material as the two are bonded.

Next, the organic film 140 is peeled off from all regions other than the formation region of the solder resist layer 403. It should be noted that masking methods or the like may instead be used to prevent film formation in these other areas.

Next, the whole is placed into the Sn plating vat and Sn plating is thus formed in predetermined regions of the wiring pattern layer 402. The Sn plating layer can be formed on conductive surfaces only by using non-electrolytic replacement plating or similar methods. The film carrier tape 40 is thus completed.

(Principal Chains of Functional Organic Molecules 14)

The functional organic molecules 14 shown in FIG. 12E are made up of a first functional group A4, a principal chain B4, and a second functional group C4, bonded in that order. However, the functional organic molecules may alternatively be made up of a first functional group A4, a principal chain B11, a principal chain B12, and a second functional group C4, bonded in that order, or else of either a principal chain B11 or a principal chain B12 with a first functional group A2 and a second functional group C4 bonded thereto.

If the functional organic molecules have a principal chain B11, then the anchor effects described for Embodiment 1 can be obtained. Also, if the functional organic molecules have a principal chain B12, then the UV protection effects described for Embodiment 3 can be obtained.

[Embodiment 8]

The explanation of Embodiment 8 is focused on the points of difference thereof with Embodiment 7.

As shown in FIGS. 13 E and 13F, the film carrier tape pertaining to the present Embodiment is made up of a wiring pattern 402 and a solder resist layer 403 with functional organic molecules 15, each having a second functional group C5 that imparts light-polymerization-initializing or photosensitizing properties, interposed therebetween.

Figure 13A:
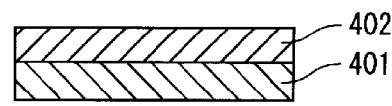
FIGS. 13A through 13F show the manufacturing processing of the film carrier tape pertaining to Embodiment 8.
Figure 13B:
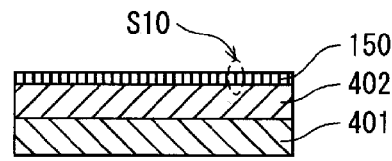
Figure 13C:
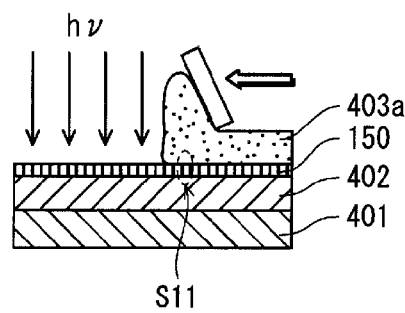
Figure 13D:
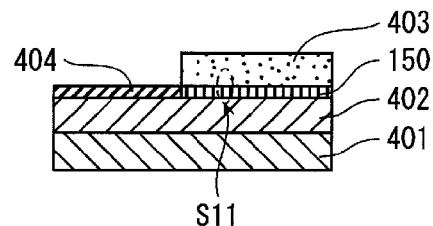
Figure 13E:
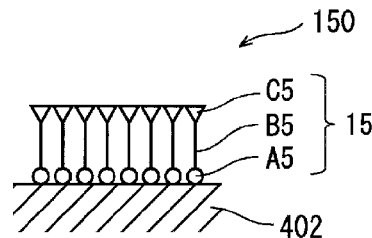
Figure 13F:
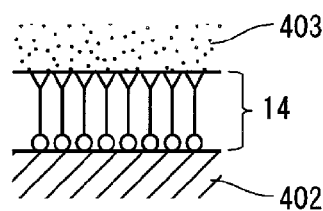

As shown in FIG. 13E, each of the functional organic molecules 15 has a principal chain B5 with a first principal group A5 able to bond with metals at one end, and a second functional group C5 at the other end. Any chemical compound, structure, or derivative thereof that includes one or more members selected from the group consisting of benzophenone, acetophenone, alkylphenone, benzoin, anthraquinone, ketal, thioxanthene, coumarin, halogenated triazine, halogenated oxydiazole, oxine ester, acridine, acridone, fluorenone, fluoran, acylphosphine oxide, metallocene, polynuclear aromatic compounds, xanthene, cyanine, squalium, acridone, titanocene, and tetraalkyl thiuram sulfide may be used as the second functional group C5. Furthermore, other compounds not listed above may also be used as long as such compounds have light-polymerization-initializing or photosensitizing properties.

The first functional group A5 is identical to the first functional group A1 and the principal chain B5 is identical to the principal chain B1 respectively explained for Embodiment 1.

In forming the organic film 150 using such functional organic molecules 15, strong bonds arise between the principal chains B4 of neighboring functional organic molecules 15. Thus, not only is peeling prevented in the solder resist layer and the wiring pattern layer 402 in the same manner as that of Embodiment 7, but also, when the solder resist layer is applied, the material is made to harden faster as the light polymerization initiator is excited. The solder resist layer can thus be formed all the sooner. As a result, liquid drops and loss of shape can be prevented from occurring, and a precise, minute pattern can be formed of the solder resist layer 403.

To be precise, the adhesiveness of the paste used for the solder resist at application processing time can be adjusted to a predetermined point and the paste then applied onto the wiring pattern layer 402 according to a predetermined pattern mask. The mask is removed after the paste so applied has dried. However, the paste may diffuse slightly after drying. For this reason, such diffusion can be accounted for and the paste applied over a slightly smaller area than that of the pattern mask. Yet, doing so makes for acute angles at the end portions of the applied paste, which in turn makes peeling more likely to ensue at plating time.

In contrast, in Embodiment 8, the organic film is irradiated with UV rays immediately before the paste as applied and the light energy (E=hv) thus imparted to the second functional groups C5 can induce earlier thermosetting in the paste. Accordingly, acute angles do not form at the end portions, as is the case conventionally. Also, given lessened paste flow, the paste can be applied more accurately with respect to the pattern mask, which approach has the merit of enabling the formation of a highly precise solder resist layer.

(Manufacturing Method)

First, a predetermined wiring pattern layer 402 (Cu foil) is formed over the insulating film 401 using photo-etching or similar methods (FIG. 13A).

Next, the functional organic molecules 15 are made to adhere to the wiring pattern layer 402 and the organic film 140 is formed through self-assembly thereof into a monomolecular film (FIG. 13B).

Next, the second functional groups C5 of the functional organic molecules that make up the organic film 140 are irradiated with UV rays of predetermined wavelengths (for example, 340 nm and up). Thus, the second functional groups C5 transition from a base state to an excited state (E0→E1). While the excited state persists, the paste that will be part of the solder resist layer is applied at a predetermined thickness using a blade BL (see FIG. 13C). Thus, the second functional groups transmit the energy of excitation to the solder resist layer as thermal energy, triggering thermosetting therein.

This completes the manufacture of the film carrier tape (see FIG. 13D).

(Principal Chains of Functional Organic Molecules 15)

As shown in FIG. 13E, the functional organic molecules 15 are made up of a first functional group A5, a principal chain B5, and a second functional group C5, bonded in that order. However, the functional organic molecules may alternatively be made up of a first functional group A5, a principal chain B11, a principal chain B12, and a second functional group C5, bonded in that order, or else of either a principal chain B11 or a principal chain B12 with a first functional group A5 and a second functional group C5 bonded thereto.

If the functional organic molecules have a principal chain B11, then the anchor effects described for Embodiment 1 can be obtained. Also, if the functional organic molecules have a principal chain B12, then the UV protection effects described for Embodiment 3 can be obtained.

[Embodiment 9]

The explanation of Embodiment 9 is focused on the points of difference thereof with Embodiments 7 and 8.

In Embodiment 9, an organic film that may be formed of the functional organic molecules 15 explained above for Embodiment 8, or else the functional organic molecules used may be made up of a first functional group A5, a principal chain B11, a principal chain B12, and a second functional group C5, bonded in that order, or else of either a principal chain B11 or a principal chain B12 with a first functional group A5 and a second functional group C5 bonded thereto. This organic film is formed over the wiring pattern 402, but is characterized by the use of a batch method for the formation of the solder resist layer 403.

Accordingly, strengthened bonding can be obtained between the solder resist layer 403 and the wiring pattern layer 402 in the same manner as Embodiment 8. In addition, the thickness of the solder resist layer 403 can be prepared over a wider range than is possible using ordinary printing methods. This has the merit of flexibility in accommodating changes in design.

FIGS. 14A through 14E show the manufacturing process of the film carrier tape 40.

Figure 14A:
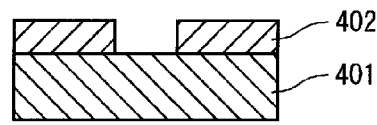
FIGS. 14A through 14E show the manufacturing processing of the film carrier tape pertaining to Embodiment 9.

First, a predetermined wiring pattern layer 402 is formed over the insulating film 401 (FIG. 14A).

Figure 14B:
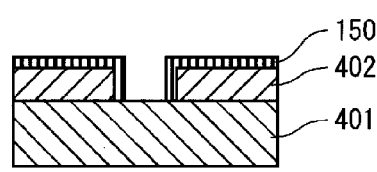

Next, the functional organic molecules are made to form the organic film 150 over the surface of the wiring pattern layer 402 to obtain an intermediate product. This constitutes the organic film formation processing (FIG. 14B). This film formation can be performed in the same manner as that explained for Embodiment 1.

Next, a resin dispersion fluid is prepared in which a light polymerizing compound that will form the solder resist material has been dispersed by a solvent. Any monomer or oligomer selected from the group consisting of a compound with an acrylate group in the molecule, a compound including a methacrylate group in the molecule, a compound with an acryl amide group in the molecule, a compound with an urethane group in the molecule, a compound with an isocyanate group in the molecule, a compound with a vinyl group in the molecule and the like may be used as the light polymerizing compound. The resin dispersion fluid so prepared fills a batch.

A pattern mask PM is placed on the above-described intermediate product so as to fit regions where the solder resist layer 403 is to be formed. A photo-resist layer formed through known exposure techniques may, for instance, be used for the pattern mask PM.

Figure 14C:
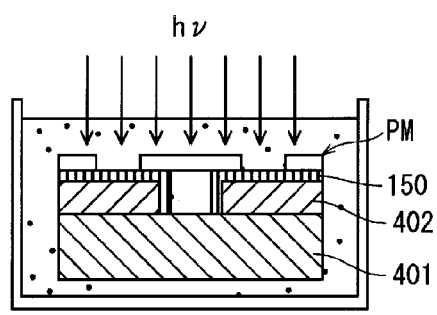

Through immersion in the resin dispersion fluid of the above-described batch, liquid stability is preserved and solder resist layer formation processing is realized by irradiation thereof with external UV rays (see FIG. 14C).

To be precise, in the neighborhood of the organic film 150 at the aperture of the pattern mask PM (or pattern gap for a photo-resist layer), a polymerization reaction occurs in the light polymerizing compounds dispersed in the liquid with the second functional groups C5, which have light-polymerization-initializing properties, at the center. The polymerization reaction progresses from contact positions with the second functional groups C5. Thus, if the UV ray irradiation time is kept extremely short, then a solder resist layer 403 of monomolecular thickness is formed. On the other hand, if a longer irradiation period is used, then a solder resist layer 403 of a thickness corresponding to the liquid depth of the second functional groups C5 will theoretically result. As such, the above method allows the thickness of the solder resist layer 403 to be adjusted.

The thickness of the solder resist layer 403 can be adjusted not only through the length of the UV ray irradiation period but also through control of the dispersion concentration of the compounds in the dispersion fluid.

Figure 14D:
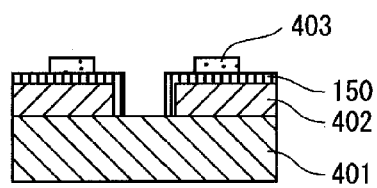

After the hardening reaction by UV rays, the intermediate product is removed from the batch, the mask is removed, and necessary washing is performed (see FIG. 14D).

Figure 14E:
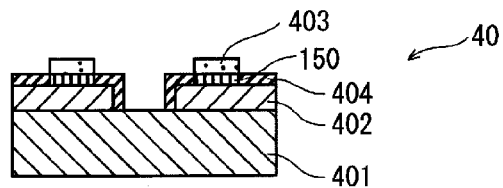
Figure 15A:
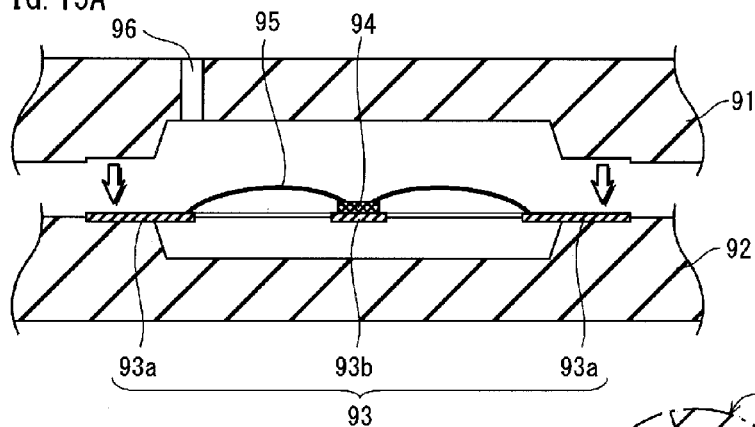
FIGS. 15A through 15D show the injection-molding time processing for a conventional semiconductor device.
Figure 15B:
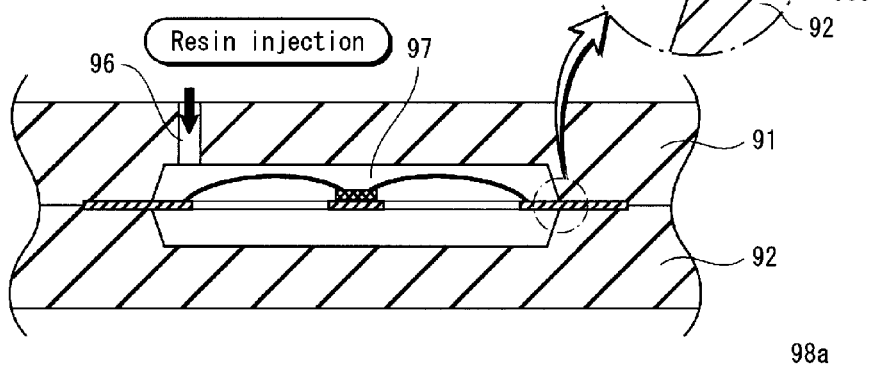
Figure 15C:
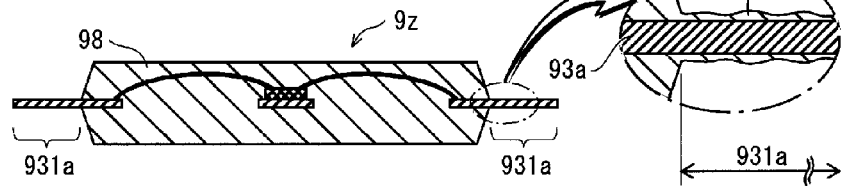
Figure 15D:
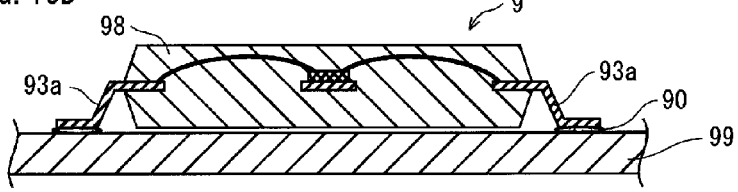

Afterward, the organic film 150 is removed from regions other than that under the solder resist layer 403, and the Sn plating 404 is formed (see FIG. 14E).

This concludes the manufacturing process of the film carrier tape 40.

According to this manufacturing method, buoyancy is imparted by relative density differences within the dispersion fluid such that the solder resist layer 403 formed over the organic film 150 will harden quickly without experiencing deformation under gravity. This has the merits of allowing free formation of a solder resist layer 403 that may be thicker or thinner depending on the precise shape and thickness of the pattern.

The relative density of the dispersion fluid should ideally be such that the light polymerizing compounds become well-dispersed in a fixed period. Furthermore, if the relative densities within the dispersion fluid are such that the light polymerizing compounds gradually sink, then local light polymerizing compound shortages can be prevented near the second functional groups at polymerization time.

(Miscellaneous)

In each of the above-described Embodiments, the organic film is described as a monomolecular film made up of functional organic molecules. However, a multi-layer film may also be used as long as the adhesive strength with the mounting substrate of the semiconductor device and the like is not negatively affected.

In such a case, neighboring second functional groups and first functional groups will be required to form bonds between first and second layers made up of the functional organic molecules. That is, the first functional group must be able to bond with the metal of the lead unit, die-pads, and the like as well as with the second functional group.

Also, the functional organic molecules of the present invention may be made up of any combination of first functional groups, second functional groups, and principal chains described as examples in each of the Embodiments, so long as no contradictions result with regard to the functions thereof. That is, the structure of the functional organic molecules is not limited to the chemical structure of the functional groups and so on shown in each of the above Embodiments, but may also be a combination of chemical structures from each of the Embodiments.

INDUSTRIAL APPLICABILITY

The present invention can be expected to be useful in semiconductor devices consisting of IC, LSI, or VLSI packaged using sealing resin, as well as in LED devices using an LED for LED lighting devices, and in film carrier tape or the like used in flexible substrates and the like.

REFERENCE SIGNS LIST

A1-A5 first functional group
B1-B5 principal chain
B11, B12 principal chain
C1-C5, C2' second functional group
3 leads
3*a*, 3*b* die-pads
10 semiconductor device (QFP)
11-17, 12*a* functional organic molecules
21 molded resin
22 reflector
30 lead unit
31 LED device
40 film carrier tape
42 LED chip
63 Ag plating
82*a* overflow resin
110, 120, 120*a*, 130, 140, 150 organic film
301, 302 exposed regions
301*a* outer leads
302*a* inner leads
401 insulating film
402 wiring pattern layer
403*x* end portions

404 Sn plating
406 erosion region
408 Sn accumulative layer

The invention claimed is:

1. An organic compound forming a self-assembling film by aligning an extremity of a principal chain on a metal surface, wherein:
   the principal chain comprises a N-containing heterocycle containing two or more N atoms,
   the N-containing heterocycle comprises one or more compounds selected from the group consisting of imidazole, triazole, tetrazole, oxadiazole, thiadiazole, pyrimidine, pyridazine, pyrazine, and triazine,
   the principal chain further comprises, farther from the extremity thereof than the N-containing heterocycle, one or more skeletons selected from the group consisting of an aryl skeleton, a pyrene skeleton, a phenanthrene skeleton, and a fluorene skeleton,
   the number of aromatic rings included in the one or more skeletons is from two to six, and
   the aryl skeleton is selected from the group consisting of biphenyl, terphenyl, quaterphenyl, quinquiphenyl, and sexiphenyl.

* * * * *